(12) United States Patent
Stone et al.

(10) Patent No.: US 7,905,903 B2
(45) Date of Patent: *Mar. 15, 2011

(54) METHOD FOR TISSUE FIXATION

(75) Inventors: Kevin T. Stone, Winona Lake, IN (US); Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 534 days.

This patent is subject to a terminal disclaimer.

(21) Appl. No.: 11/935,681

(22) Filed: Nov. 6, 2007

(65) Prior Publication Data

US 2008/0065114 A1 Mar. 13, 2008

Related U.S. Application Data

(63) Continuation-in-part of application No. 11/347,661, filed on Feb. 3, 2006, now Pat. No. 7,749,250.

(51) Int. Cl.
*A61B 17/04* (2006.01)
(52) U.S. Cl. ....................................... 606/232
(58) Field of Classification Search ................... 606/300, 606/74, 103, 232, 223–228, 233, 60; 289/2, 289/17; 24/129 D, 115 H, 122.3, 131 C, 24/115 A
See application file for complete search history.

(56) References Cited

U.S. PATENT DOCUMENTS

| 26,501 | A | 10/1859 | Kendrick et al. |
| 65,499 | A | 6/1867 | Miller |
| 126,366 | A | 4/1872 | Wills |
| 233,475 | A | 10/1880 | Cook et al. |
| 261,501 | A | 7/1882 | Vandermark |
| 417,805 | A | 12/1889 | Beaman |
| 487,304 | A | 12/1892 | Todd |
| 762,710 | A | 6/1901 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,635,066 | A | 7/1927 | Wells |
| 401,677 | A | 11/1933 | Roeder |
| 1,950,799 | A | 3/1934 | Jones |

(Continued)

FOREIGN PATENT DOCUMENTS

AU 4957264 3/1966

(Continued)

OTHER PUBLICATIONS

"EZ Loc Femoral Fixation Device," copyright 2005 Arthrotek, Inc. (8 sheets). "PANALOK Anchor with PDS II and ETHIBOND Suture", Mitek Products ETHICON, 1997.
"SE Graft Tensioning System Surgical Technique," Linvatec Corporation copyright 2003, 2004.

(Continued)

*Primary Examiner* — (Jackie) Tan-Uyen T Ho
*Assistant Examiner* — Dianne Dornbusch
(74) *Attorney, Agent, or Firm* — Harness, Dickey

(57) ABSTRACT

A method for securing a strand to a fixation member for arthroscopic fixation, wherein the fixation member includes an aperture therethrough. The method includes passing a strand having first and second ends through a flexible sleeve, passing the sleeve through the aperture of the fixation member in a first direction, tensioning the strand, and pulling the sleeve in a second direction different than the first direction to secure the sleeve to the fixation member without tying the strand on the fixation member.

25 Claims, 9 Drawing Sheets

U.S. PATENT DOCUMENTS

| | | |
|---|---|---|
| 2,065,659 A | 12/1936 | Cullen |
| 2,108,206 A | 2/1938 | Meeker |
| 2,121,193 A | 6/1938 | Hanicke |
| 2,242,003 A | 5/1941 | Lorenzo |
| 2,267,925 A | 12/1941 | Johnston |
| 2,302,986 A | 11/1942 | Vollrath |
| 2,329,398 A | 9/1943 | Duffy |
| RE22,857 E | 3/1947 | Ogburn |
| 2,526,959 A | 10/1950 | Lorenzo |
| 2,528,456 A | 10/1950 | Stevenson |
| 2,562,419 A | 7/1951 | Ferris |
| 2,581,564 A | 1/1952 | Villegas |
| 2,600,395 A | 6/1952 | Domoj et al. |
| 2,610,631 A | 9/1952 | Calicchio |
| 2,665,597 A | 1/1954 | Hill |
| 2,669,774 A | 2/1954 | Mitchell |
| 2,698,986 A | 1/1955 | Brown |
| 2,760,488 A | 8/1956 | Pierce |
| 2,833,284 A | 5/1958 | Springer |
| 2,846,712 A | 8/1958 | Markman |
| 2,860,393 A | 11/1958 | Brock |
| 2,880,728 A | 4/1959 | Rights |
| 2,881,762 A | 4/1959 | Lowrie |
| 2,883,096 A | 4/1959 | Dawson |
| 2,913,042 A | 11/1959 | Taylor |
| 3,000,009 A | 9/1961 | Selstad |
| 3,003,155 A | 10/1961 | Mielzynski et al. |
| 3,013,559 A | 12/1961 | Thomas |
| 3,037,619 A | 6/1962 | Stevans |
| 3,039,460 A | 9/1962 | Chandler |
| 3,090,386 A | 5/1963 | Curtis |
| 3,103,666 A | 9/1963 | Bone |
| 3,123,077 A | 3/1964 | Alcamo |
| 3,125,095 A | 3/1964 | Kaufman et al. |
| 3,209,422 A | 10/1965 | Dritz |
| 3,234,938 A | 2/1966 | Robinson |
| 3,240,379 A | 3/1966 | Bremer et al. |
| 3,250,271 A | 5/1966 | Lippes |
| 3,399,432 A | 9/1968 | Merser |
| 3,409,014 A | 11/1968 | Shannon |
| RE26,501 E | 12/1968 | Kendrick et al. |
| 3,435,475 A | 4/1969 | Bisk |
| 3,467,089 A | 9/1969 | Hasson |
| 3,470,834 A | 10/1969 | Bone |
| 3,470,875 A | 10/1969 | Johnson |
| 3,500,820 A | 3/1970 | Almen |
| 3,507,274 A | 4/1970 | Soichet |
| 3,513,484 A | 5/1970 | Hausner |
| 3,515,132 A | 6/1970 | McKnight |
| 3,522,803 A | 8/1970 | Majzlin |
| 3,527,223 A | 9/1970 | Shein |
| 3,533,406 A | 10/1970 | Hutterer et al. |
| 3,541,591 A | 11/1970 | Hoegerman |
| 3,547,389 A | 12/1970 | Mitchell |
| 3,579,831 A | 5/1971 | Stevens et al. |
| 3,590,616 A | 7/1971 | Schussler et al. |
| 3,608,095 A | 9/1971 | Barry |
| 3,618,447 A | 11/1971 | Goins |
| 3,628,530 A | 12/1971 | Schwartz |
| 3,643,649 A | 2/1972 | Amato |
| 3,648,705 A | 3/1972 | Lary |
| 3,656,483 A | 4/1972 | Rudel |
| 3,664,345 A | 5/1972 | Dabbs et al. |
| 3,665,560 A | 5/1972 | Bennett et al. |
| 3,675,639 A | 7/1972 | Cimber |
| 3,683,422 A | 8/1972 | Stemmer et al. |
| 3,692,022 A | 9/1972 | Ewing |
| 3,695,271 A | 10/1972 | Chodorow |
| 3,699,969 A | 10/1972 | Allen |
| 3,716,058 A | 2/1973 | Tanner, Jr. |
| 3,744,488 A | 7/1973 | Cox |
| 3,752,516 A | 8/1973 | Mumma |
| 3,757,629 A | 9/1973 | Schneider |
| 3,763,856 A | 10/1973 | Blomberg |
| 3,771,520 A | 11/1973 | Lerner |
| 3,777,748 A | 12/1973 | Abramson |
| 3,807,407 A | 4/1974 | Schweizer |
| 3,825,010 A | 7/1974 | McDonald |
| 3,840,017 A | 10/1974 | Violante et al. |
| 3,842,824 A | 10/1974 | Neufeld |
| 3,842,840 A | 10/1974 | Schweizer |
| 3,845,772 A | 11/1974 | Smith |
| 3,867,933 A | 2/1975 | Kitrilakis |
| 3,867,944 A | 2/1975 | Samuels |
| 3,871,368 A | 3/1975 | Johnson et al. |
| 3,871,379 A | 3/1975 | Clarke |
| 3,874,388 A | 4/1975 | King et al. |
| 3,875,648 A | 4/1975 | Bone |
| 3,877,570 A | 4/1975 | Barry |
| 3,880,156 A | 4/1975 | Hoff |
| 3,881,475 A | 5/1975 | Gordon et al. |
| 3,889,666 A | 6/1975 | Lerner |
| 3,892,240 A | 7/1975 | Park |
| 3,896,500 A | 7/1975 | Rambert et al. |
| 3,907,442 A | 9/1975 | Reid |
| 3,910,281 A | 10/1975 | Kletschka et al. |
| 3,918,444 A | 11/1975 | Hoff et al. |
| 3,918,455 A | 11/1975 | Coplan |
| 3,927,666 A | 12/1975 | Hoff |
| 3,931,667 A | 1/1976 | Merser et al. |
| 3,933,153 A | 1/1976 | Csatary et al. |
| 3,937,217 A | 2/1976 | Kosonen et al. |
| 3,943,932 A | 3/1976 | Woo |
| 3,946,728 A | 3/1976 | Bettex et al. |
| 3,946,740 A | 3/1976 | Bassett |
| 3,953,896 A | 5/1976 | Treace |
| 3,954,103 A | 5/1976 | Garcia-Roel et al. |
| 3,961,632 A | 6/1976 | Moossun |
| 3,973,560 A | 8/1976 | Emmett et al. |
| 3,976,079 A | 8/1976 | Samuels et al. |
| 3,977,050 A | 8/1976 | Perez et al. |
| 3,979,799 A | 9/1976 | Merser et al. |
| 3,985,138 A | 10/1976 | Jarvik |
| 3,990,619 A | 11/1976 | Russell |
| 4,005,707 A | 2/1977 | Moulding, Jr. |
| 4,006,747 A | 2/1977 | Kronenthal et al. |
| 4,007,743 A | 2/1977 | Blake |
| 4,013,071 A | 3/1977 | Rosenberg et al. |
| 4,026,281 A | 5/1977 | Mayberry et al. |
| 4,050,100 A | 9/1977 | Barry |
| 4,054,954 A | 10/1977 | Nakayama et al. |
| 4,085,466 A | 4/1978 | Goodfellow et al. |
| 4,094,313 A | 6/1978 | Komamura et al. |
| 4,103,690 A | 8/1978 | Harris |
| RE29,819 E | 10/1978 | Bone |
| 4,121,487 A | 10/1978 | Bone |
| 4,143,656 A | 3/1979 | Holmes et al. |
| 4,144,876 A | 3/1979 | DeLeo |
| 4,149,277 A | 4/1979 | Bokros |
| 4,157,714 A | 6/1979 | Foltz et al. |
| 4,160,453 A | 7/1979 | Miller |
| 4,164,225 A | 8/1979 | Johnson et al. |
| 4,172,458 A | 10/1979 | Pereyra |
| 4,175,555 A | 11/1979 | Herbert et al. |
| 4,185,636 A | 1/1980 | Gabbay et al. |
| 4,196,883 A | 4/1980 | Einhorn et al. |
| 4,210,148 A | 7/1980 | Stivala |
| 4,235,161 A | 11/1980 | Kunreuther |
| 4,235,238 A | 11/1980 | Ogiu et al. |
| 4,237,779 A | 12/1980 | Kunreuther |
| 4,243,037 A | 1/1981 | Smith |
| 4,249,525 A | 2/1981 | Krzeminski |
| 4,263,913 A | 4/1981 | Malmin |
| 4,265,246 A | 5/1981 | Barry |
| 4,273,117 A | 6/1981 | Neuhauser et al. |
| 4,275,717 A | 6/1981 | Bolesky |
| 4,287,807 A | 9/1981 | Pacharis et al. |
| 4,291,698 A | 9/1981 | Fuchs et al. |
| 4,301,551 A | 11/1981 | Dore et al. |
| 4,312,337 A | 1/1982 | Donohue |
| 4,316,469 A | 2/1982 | Kapitanov et al. |
| 4,326,531 A | 4/1982 | Shimonaka et al. |
| 4,345,601 A | 8/1982 | Fukuda |
| 4,349,027 A | 9/1982 | DiFrancesco |
| 4,388,921 A | 6/1983 | Sutter et al. |
| 4,400,833 A | 8/1983 | Kurland |
| 4,402,445 A | 9/1983 | Green |

| | | | | | |
|---|---|---|---|---|---|
| 4,409,974 A | 10/1983 | Freedland | 4,828,562 A | 5/1989 | Kenna |
| 4,438,769 A | 3/1984 | Pratt et al. | 4,832,026 A | 5/1989 | Jones |
| 4,441,489 A | 4/1984 | Evans et al. | 4,834,098 A | 5/1989 | Jones |
| 4,454,875 A | 6/1984 | Pratt et al. | 4,838,282 A | 6/1989 | Strasser et al. |
| 4,462,395 A | 7/1984 | Johnson | 4,841,960 A | 6/1989 | Garner |
| 4,463,753 A | 8/1984 | Gustilo | 4,851,005 A | 7/1989 | Hunt et al. |
| 4,473,102 A | 9/1984 | Ohman et al. | 4,858,608 A | 8/1989 | McQuilkin et al. |
| 4,484,570 A | 11/1984 | Sutter et al. | 4,860,513 A | 8/1989 | Whitman |
| 4,493,323 A | 1/1985 | Albright et al. | 4,863,383 A | 9/1989 | Grafelmann et al. |
| 4,496,468 A | 1/1985 | House et al. | 4,870,957 A | 10/1989 | Goble et al. |
| 4,505,274 A | 3/1985 | Speelman | 4,873,976 A | 10/1989 | Schreiber |
| 4,509,516 A | 4/1985 | Richmond | 4,887,601 A | 12/1989 | Richards |
| 4,531,522 A | 7/1985 | Bedi et al. | 4,890,615 A | 1/1990 | Caspari et al. |
| 4,532,926 A | 8/1985 | O'Holla | 4,893,619 A | 1/1990 | Dale et al. |
| 4,534,350 A | 8/1985 | Golden et al. | 4,893,974 A | 1/1990 | Fischer et al. |
| 4,535,764 A | 8/1985 | Ebert | 4,895,148 A | 1/1990 | Bays et al. |
| 4,537,185 A | 8/1985 | Stednitz | 4,896,668 A | 1/1990 | Popoff et al. |
| 4,549,652 A | 10/1985 | Free | 4,898,156 A | 2/1990 | Gatturna et al. |
| 4,561,432 A | 12/1985 | Mazor | 4,899,743 A | 2/1990 | Nicholson et al. |
| 4,564,007 A | 1/1986 | Coombs et al. | 4,901,721 A | 2/1990 | Hakki |
| 4,570,623 A | 2/1986 | Ellison et al. | 4,923,461 A | 5/1990 | Caspari et al. |
| 4,573,844 A | 3/1986 | Smith | 4,927,421 A | 5/1990 | Goble et al. |
| 4,576,608 A | 3/1986 | Homsy | 4,946,468 A | 8/1990 | Li |
| 4,584,722 A | 4/1986 | Levy et al. | 4,950,270 A | 8/1990 | Bowman et al. |
| 4,590,928 A | 5/1986 | Hunt et al. | 4,950,285 A | 8/1990 | Wilk |
| 4,595,007 A | 6/1986 | Mericle | 4,960,381 A | 10/1990 | Niznick |
| 4,596,249 A | 6/1986 | Freda et al. | 4,961,741 A | 10/1990 | Hayhurst |
| 4,602,635 A | 7/1986 | Mulhollan et al. | 4,968,315 A | 11/1990 | Gatturna |
| 4,602,636 A | 7/1986 | Noiles | 4,968,317 A | 11/1990 | Tormala et al. |
| 4,604,997 A | 8/1986 | De Bastiani et al. | 4,969,886 A | 11/1990 | Cziffer et al. |
| 4,605,414 A | 8/1986 | Czajka | 4,976,736 A | 12/1990 | White et al. |
| 4,616,650 A | 10/1986 | Green et al. | 4,978,350 A | 12/1990 | Wagenknecht et al. |
| 4,621,640 A | 11/1986 | Mulhollan et al. | 4,979,956 A | 12/1990 | Silvestrini |
| 4,624,254 A | 11/1986 | McGarry et al. | 4,983,176 A | 1/1991 | Cushman et al. |
| 4,632,100 A | 12/1986 | Somers et al. | 4,988,351 A | 1/1991 | Paulos et al. |
| 4,635,637 A | 1/1987 | Schreiber | 4,994,074 A | 2/1991 | Bezwada et al. |
| 4,636,121 A | 1/1987 | Miller | 4,997,433 A | 3/1991 | Goble et al. |
| 4,641,652 A | 2/1987 | Hutterer et al. | 5,002,550 A | 3/1991 | Li |
| 4,649,952 A | 3/1987 | Jobe | 5,002,562 A | 3/1991 | Oberlander |
| 4,653,486 A | 3/1987 | Coker | 5,007,921 A | 4/1991 | Brown |
| 4,653,487 A | 3/1987 | Maale | 5,030,224 A | 7/1991 | Wright et al. |
| 4,653,489 A | 3/1987 | Tronzo | 5,037,422 A | 8/1991 | Hayhurst et al. |
| 4,655,777 A | 4/1987 | Dunn et al. | 5,041,129 A | 8/1991 | Hayhurst et al. |
| 4,662,068 A | 5/1987 | Polonsky | 5,046,513 A | 9/1991 | Gatturna et al. |
| 4,667,662 A | 5/1987 | Titone et al. | 5,047,030 A | 9/1991 | Draenert et al. |
| 4,667,675 A | 5/1987 | Davis | 5,053,046 A | 10/1991 | Janese |
| 4,669,473 A | 6/1987 | Richards et al. | 5,053,047 A | 10/1991 | Yoon |
| 4,683,895 A | 8/1987 | Pohndorf | 5,059,201 A | 10/1991 | Asnis |
| 4,688,561 A | 8/1987 | Reese | 5,059,206 A | 10/1991 | Winters |
| 4,690,169 A | 9/1987 | Jobe | 5,062,344 A | 11/1991 | Gerker |
| 4,705,040 A | 11/1987 | Mueller et al. | 5,062,843 A | 11/1991 | Mahony, III |
| 4,708,132 A | 11/1987 | Silvestrini | 5,078,731 A | 1/1992 | Hayhurst |
| 4,716,893 A | 1/1988 | Fischer et al. | 5,078,843 A | 1/1992 | Pratt |
| 4,719,671 A | 1/1988 | Ito et al. | 5,084,050 A | 1/1992 | Draenert et al. |
| 4,719,917 A | 1/1988 | Barrows et al. | 5,084,058 A | 1/1992 | Li |
| 4,723,540 A | 2/1988 | Gilmer, Jr. | 5,085,661 A | 2/1992 | Moss |
| 4,724,839 A | 2/1988 | Bedi et al. | 5,087,263 A | 2/1992 | Li |
| 4,728,332 A | 3/1988 | Albrektsson et al. | 5,092,866 A | 3/1992 | Breard et al. |
| 4,738,255 A | 4/1988 | Goble et al. | 5,098,435 A | 3/1992 | Stednitz et al. |
| 4,741,330 A | 5/1988 | Hayhurst | 5,100,415 A | 3/1992 | Hayhurst |
| 4,741,336 A | 5/1988 | Failla et al. | 5,100,417 A | 3/1992 | Cerier et al. |
| 4,744,353 A | 5/1988 | McFarland | 5,116,337 A | 5/1992 | Johnson |
| 4,744,793 A | 5/1988 | Parr et al. | 5,116,373 A | 5/1992 | Jakob et al. |
| 4,750,492 A | 6/1988 | Jacobs | 5,116,375 A | 5/1992 | Hofmann |
| 4,760,843 A | 8/1988 | Fischer et al. | 5,123,913 A | 6/1992 | Wilk et al. |
| 4,760,848 A | 8/1988 | Hasson | 5,127,785 A | 7/1992 | Faucher et al. |
| 4,772,261 A | 9/1988 | Von Hoff et al. | 5,129,901 A | 7/1992 | Decoste |
| 4,772,286 A | 9/1988 | Goble et al. | 5,129,902 A | 7/1992 | Goble et al. |
| 4,773,910 A | 9/1988 | Chen et al. | 5,129,904 A | 7/1992 | Illi et al. |
| 4,775,380 A | 10/1988 | Seedhom et al. | 5,129,906 A | 7/1992 | Ross et al. |
| 4,776,328 A | 10/1988 | Frey et al. | 5,139,499 A | 8/1992 | Small et al. |
| 4,781,190 A | 11/1988 | Lee et al. | 5,139,520 A | 8/1992 | Rosenberg |
| 4,784,126 A | 11/1988 | Hourahane et al. | 5,143,498 A | 9/1992 | Whitman |
| 4,787,882 A | 11/1988 | Claren et al. | 5,147,362 A | 9/1992 | Goble |
| 4,790,297 A | 12/1988 | Luque et al. | 5,149,329 A | 9/1992 | Richardson |
| 4,793,363 A | 12/1988 | Ausherman et al. | 5,152,790 A | 10/1992 | Rosenberg et al. |
| 4,809,695 A | 3/1989 | Gwathmey et al. | 5,154,189 A | 10/1992 | Oberlander |
| 4,813,406 A | 3/1989 | Ogle, II | 5,156,616 A | 10/1992 | Meadows et al. |
| 4,823,794 A | 4/1989 | Pierce | 5,163,960 A | 11/1992 | Bonutti |

| | | | | | |
|---|---|---|---|---|---|
| D331,626 S | 12/1992 | Hayhurst et al. | 5,423,819 A | 6/1995 | Small et al. |
| 5,169,400 A | 12/1992 | Muhling et al. | 5,423,823 A | 6/1995 | Schmieding |
| 5,176,682 A | 1/1993 | Chow | 5,423,860 A | 6/1995 | Lizardi et al. |
| 5,178,629 A | 1/1993 | Kammerer | 5,425,733 A | 6/1995 | Schmieding |
| 5,183,458 A | 2/1993 | Marx | 5,425,766 A | 6/1995 | Bowald et al. |
| 5,192,282 A | 3/1993 | Draenert et al. | 5,433,751 A | 7/1995 | Christel et al. |
| 5,197,987 A | 3/1993 | Koch et al. | 5,437,680 A | 8/1995 | Yoon |
| 5,203,784 A | 4/1993 | Ross et al. | 5,439,684 A | 8/1995 | Prewett et al. |
| 5,203,787 A | 4/1993 | Noblitt et al. | 5,443,468 A | 8/1995 | Johnson |
| 5,207,679 A | 5/1993 | Li | 5,443,482 A | 8/1995 | Stone et al. |
| 5,209,753 A | 5/1993 | Biedermann et al. | 5,443,483 A | 8/1995 | Kirsch et al. |
| 5,209,805 A | 5/1993 | Spraggins | 5,443,509 A | 8/1995 | Boucher et al. |
| 5,211,647 A | 5/1993 | Schmieding | 5,445,833 A | 8/1995 | Badylak et al. |
| 5,211,650 A | 5/1993 | Noda | 5,447,512 A | 9/1995 | Wilson et al. |
| 5,214,987 A | 6/1993 | Fenton, Sr. | 5,451,203 A | 9/1995 | Lamb |
| 5,219,359 A | 6/1993 | McQuilkin et al. | 5,454,811 A | 10/1995 | Huebner |
| 5,224,946 A | 7/1993 | Hayhurst et al. | 5,456,685 A | 10/1995 | Huebner |
| 5,230,699 A | 7/1993 | Grasinger | 5,456,722 A | 10/1995 | McLeod et al. |
| 5,232,436 A | 8/1993 | Janevski | 5,458,601 A | 10/1995 | Young, Jr. et al. |
| 5,234,435 A | 8/1993 | Seagrave, Jr. | 5,458,604 A | 10/1995 | Schmieding |
| 5,235,238 A | 8/1993 | Nomura et al. | 5,462,560 A | 10/1995 | Stevens |
| 5,236,445 A | 8/1993 | Hayhurst et al. | 5,464,426 A | 11/1995 | Bonutti |
| 5,236,461 A | 8/1993 | Forte | 5,464,427 A | 11/1995 | Curtis et al. |
| 5,242,447 A | 9/1993 | Borzone | 5,464,440 A | 11/1995 | Johansson et al. |
| 5,246,441 A | 9/1993 | Ross et al. | 5,466,237 A | 11/1995 | Byrd, III et al. |
| 5,249,899 A | 10/1993 | Wilson | 5,467,786 A | 11/1995 | Allen et al. |
| 5,258,015 A | 11/1993 | Li et al. | 5,470,334 A | 11/1995 | Ross et al. |
| 5,258,016 A | 11/1993 | DiPoto et al. | 5,470,337 A | 11/1995 | Moss |
| 5,258,040 A | 11/1993 | Bruchman et al. | 5,470,338 A | 11/1995 | Whitfield et al. |
| 5,268,001 A | 12/1993 | Nicholson et al. | 5,472,452 A | 12/1995 | Trott |
| 5,269,160 A | 12/1993 | Wood | 5,474,565 A | 12/1995 | Trott |
| 5,269,783 A | 12/1993 | Sander | 5,474,568 A | 12/1995 | Scott |
| 5,269,809 A * | 12/1993 | Hayhurst et al. ............... 606/232 | 5,474,572 A | 12/1995 | Hayhurst |
| 5,281,422 A | 1/1994 | Badylak et al. | 5,478,344 A | 12/1995 | Stone et al. |
| 5,282,809 A | 2/1994 | Kammerer et al. | 5,478,345 A | 12/1995 | Stone et al. |
| 5,282,832 A | 2/1994 | Toso et al. | 5,480,403 A | 1/1996 | Lee et al. |
| 5,285,040 A | 2/1994 | Brandberg et al. | 5,480,406 A | 1/1996 | Nolan et al. |
| 5,290,217 A | 3/1994 | Campos | 5,484,442 A | 1/1996 | Melker et al. |
| 5,306,301 A | 4/1994 | Graf et al. | 5,486,197 A | 1/1996 | Le et al. |
| 5,312,422 A | 5/1994 | Trott | 5,490,750 A | 2/1996 | Gundy |
| 5,312,438 A | 5/1994 | Johnson | 5,496,331 A | 3/1996 | Xu et al. |
| 5,318,577 A | 6/1994 | Li | 5,496,348 A | 3/1996 | Bonutti |
| 5,318,578 A | 6/1994 | Hasson | 5,500,000 A | 3/1996 | Feagin et al. |
| 5,320,115 A | 6/1994 | Kenna | 5,505,736 A | 4/1996 | Reimels et al. |
| 5,320,626 A | 6/1994 | Schmieding | 5,507,754 A | 4/1996 | Green et al. |
| 5,320,633 A | 6/1994 | Allen et al. | 5,520,691 A | 5/1996 | Branch |
| 5,324,308 A | 6/1994 | Pierce | 5,520,702 A | 5/1996 | Sauer et al. |
| 5,334,204 A | 8/1994 | Clewett et al. | 5,522,817 A | 6/1996 | Sander et al. |
| 5,336,229 A | 8/1994 | Noda | 5,522,820 A | 6/1996 | Caspari et al. |
| 5,336,231 A | 8/1994 | Adair | 5,522,844 A | 6/1996 | Johnson |
| 5,336,240 A | 8/1994 | Metzler et al. | 5,522,845 A | 6/1996 | Wenstrom, Jr. |
| 5,342,369 A | 8/1994 | Harryman, II | 5,522,846 A | 6/1996 | Bonutti |
| 5,346,462 A | 9/1994 | Barber | 5,524,946 A | 6/1996 | Thompson |
| 5,354,298 A | 10/1994 | Lee et al. | 5,527,321 A | 6/1996 | Hinchliffe |
| 5,356,413 A | 10/1994 | Martins et al. | 5,527,342 A | 6/1996 | Pietrzak et al. |
| 5,358,511 A | 10/1994 | Gatturna et al. | 5,527,343 A | 6/1996 | Bonutti |
| 5,360,431 A | 11/1994 | Puno et al. | 5,534,012 A | 7/1996 | Bonutti |
| 5,362,294 A | 11/1994 | Seitzinger | 5,540,718 A | 7/1996 | Bartlett |
| 5,364,400 A | 11/1994 | Rego, Jr. et al. | 5,545,178 A | 8/1996 | Kensey et al. |
| 5,368,599 A | 11/1994 | Hirsch et al. | 5,545,228 A | 8/1996 | Kambin |
| 5,370,661 A | 12/1994 | Branch | 5,549,613 A | 8/1996 | Goble et al. |
| 5,370,662 A | 12/1994 | Stone et al. | 5,549,617 A | 8/1996 | Green et al. |
| 5,372,146 A | 12/1994 | Branch | 5,549,630 A | 8/1996 | Bonutti |
| 5,372,604 A | 12/1994 | Trott | 5,549,631 A | 8/1996 | Bonutti |
| 5,372,821 A | 12/1994 | Badylak et al. | 5,562,683 A | 10/1996 | Chan |
| 5,374,268 A | 12/1994 | Sander | 5,562,685 A | 10/1996 | Mollenauer et al. |
| 5,379,492 A | 1/1995 | Glesser | 5,562,686 A | 10/1996 | Sauer et al. |
| 5,383,878 A | 1/1995 | Roger et al. | 5,569,305 A | 10/1996 | Bonutti |
| 5,383,904 A | 1/1995 | Totakura et al. | 5,571,090 A | 11/1996 | Sherts |
| 5,391,171 A | 2/1995 | Schmieding | 5,571,139 A | 11/1996 | Jenkins, Jr. |
| 5,391,176 A | 2/1995 | de la Torre | 5,572,655 A | 11/1996 | Tuljapurkar et al. |
| 5,393,302 A | 2/1995 | Clark et al. | 5,573,286 A | 11/1996 | Rogozinski |
| RE34,871 E | 3/1995 | McGuire et al. | 5,573,548 A | 11/1996 | Nazre et al. |
| 5,397,356 A | 3/1995 | Goble et al. | 5,578,057 A | 11/1996 | Wenstrom, Jr. |
| 5,403,328 A | 4/1995 | Shallman | 5,584,695 A | 12/1996 | Lal Sachdeva et al. |
| 5,403,329 A | 4/1995 | Hinchcliffe | 5,584,835 A | 12/1996 | Greenfield |
| 5,403,348 A | 4/1995 | Bonutti | 5,584,836 A | 12/1996 | Ballintyn et al. |
| 5,417,691 A | 5/1995 | Hayhurst | 5,584,862 A | 12/1996 | Bonutti |
| 5,417,712 A | 5/1995 | Whittaker et al. | 5,586,986 A | 12/1996 | Hinchliffe |

| Patent | Date | Inventor |
|---|---|---|
| 5,588,575 A | 12/1996 | Davignon |
| 5,591,180 A | 1/1997 | Hinchliffe |
| 5,591,181 A | 1/1997 | Stone et al. |
| 5,591,207 A | 1/1997 | Coleman |
| 5,593,407 A | 1/1997 | Reis et al. |
| 5,593,425 A | 1/1997 | Bonutti et al. |
| 5,601,557 A | 2/1997 | Hayhurst |
| 5,601,559 A | 2/1997 | Melker et al. |
| 5,601,571 A | 2/1997 | Moss |
| 5,603,716 A | 2/1997 | Morgan et al. |
| 5,607,429 A | 3/1997 | Hayano et al. |
| 5,618,290 A | 4/1997 | Toy et al. |
| 5,628,756 A | 5/1997 | Barker, Jr. et al. |
| 5,628,766 A | 5/1997 | Johnson |
| 5,630,824 A | 5/1997 | Hart |
| 5,632,748 A | 5/1997 | Beck, Jr. et al. |
| 5,641,256 A | 6/1997 | Gundy |
| 5,643,266 A | 7/1997 | Li |
| 5,643,269 A | 7/1997 | Harle et al. |
| 5,643,320 A | 7/1997 | Lower et al. |
| 5,643,321 A | 7/1997 | McDevitt |
| 5,645,546 A | 7/1997 | Fard |
| 5,645,547 A | 7/1997 | Coleman |
| 5,645,568 A | 7/1997 | Chervitz et al. |
| 5,645,588 A | 7/1997 | Graf et al. |
| 5,647,874 A | 7/1997 | Hayhurst |
| 5,649,963 A | 7/1997 | McDevitt |
| 5,658,289 A | 8/1997 | Boucher et al. |
| 5,658,299 A | 8/1997 | Hart |
| 5,658,313 A | 8/1997 | Thal |
| 5,662,658 A | 9/1997 | Wenstrom, Jr. |
| 5,662,663 A | 9/1997 | Shallman |
| 5,665,112 A | 9/1997 | Thal |
| 5,667,513 A | 9/1997 | Torrie et al. |
| 5,671,695 A | 9/1997 | Schroeder |
| 5,674,224 A | 10/1997 | Howell et al. |
| 5,679,723 A | 10/1997 | Cooper et al. |
| 5,681,352 A | 10/1997 | Clancy, III et al. |
| 5,683,419 A | 11/1997 | Thal |
| 5,688,285 A | 11/1997 | Yamada et al. |
| 5,690,676 A | 11/1997 | DiPoto et al. |
| 5,690,678 A | 11/1997 | Johnson |
| 5,695,497 A | 12/1997 | Stahelin et al. |
| 5,697,929 A | 12/1997 | Mellinger |
| 5,699,657 A | 12/1997 | Paulson |
| 5,702,397 A | 12/1997 | Goble et al. |
| 5,702,422 A | 12/1997 | Stone |
| 5,702,462 A | 12/1997 | Oberlander |
| 5,707,373 A | 1/1998 | Sevrain et al. |
| 5,713,005 A | 1/1998 | Proebsting |
| 5,713,904 A | 2/1998 | Errico et al. |
| 5,713,905 A | 2/1998 | Goble et al. |
| 5,713,921 A | 2/1998 | Bonutti |
| 5,716,359 A | 2/1998 | Ojima et al. |
| 5,718,717 A | 2/1998 | Bonutti |
| 5,720,765 A | 2/1998 | Thal |
| 5,720,766 A | 2/1998 | Zang et al. |
| 5,725,549 A | 3/1998 | Lam |
| 5,725,556 A | 3/1998 | Moser et al. |
| 5,725,581 A | 3/1998 | Brånemark et al. |
| 5,726,722 A | 3/1998 | Uehara et al. |
| 5,728,107 A | 3/1998 | Zlock et al. |
| 5,728,109 A | 3/1998 | Schulze et al. |
| 5,728,136 A | 3/1998 | Thal |
| 5,733,293 A | 3/1998 | Scirica et al. |
| 5,733,306 A | 3/1998 | Bonutti |
| 5,733,307 A | 3/1998 | Dinsdale |
| 5,735,875 A | 4/1998 | Bonutti et al. |
| 5,741,259 A | 4/1998 | Chan |
| 5,741,281 A | 4/1998 | Martin et al. |
| 5,743,912 A | 4/1998 | Lahille et al. |
| 5,746,751 A | 5/1998 | Sherts |
| 5,746,752 A | 5/1998 | Burkhart |
| 5,746,754 A | 5/1998 | Chan |
| 5,749,898 A | 5/1998 | Schulze et al. |
| 5,755,729 A | 5/1998 | de la Torre et al. |
| 5,766,176 A | 6/1998 | Duncan |
| 5,766,250 A | 6/1998 | Chervitz et al. |
| 5,769,894 A | 6/1998 | Ferragamo |
| 5,769,899 A | 6/1998 | Schwartz et al. |
| 5,772,673 A | 6/1998 | Cuny et al. |
| 5,776,196 A | 7/1998 | Matsuzaki et al. |
| 5,782,862 A | 7/1998 | Bonutti |
| 5,782,864 A | 7/1998 | Lizardi |
| 5,782,866 A | 7/1998 | Wenstrom, Jr. |
| 5,785,714 A | 7/1998 | Morgan et al. |
| 5,792,142 A | 8/1998 | Galitzer |
| 5,792,149 A | 8/1998 | Sherts et al. |
| 5,796,127 A | 8/1998 | Hayafuji et al. |
| 5,797,928 A | 8/1998 | Kogasaka et al. |
| 5,800,407 A | 9/1998 | Eldor et al. |
| 5,810,824 A | 9/1998 | Chan |
| 5,810,848 A | 9/1998 | Hayhurst |
| 5,814,069 A | 9/1998 | Schulze et al. |
| 5,814,070 A | 9/1998 | Borzone et al. |
| 5,814,072 A | 9/1998 | Bonutti |
| 5,814,073 A | 9/1998 | Bonutti |
| 5,823,980 A | 10/1998 | Kopfer |
| 5,824,011 A | 10/1998 | Stone et al. |
| 5,843,084 A | 12/1998 | Hart et al. |
| 5,845,645 A | 12/1998 | Bonutti |
| 5,846,254 A | 12/1998 | Schulze et al. |
| 5,848,983 A | 12/1998 | Basaj et al. |
| 5,860,973 A | 1/1999 | Michelson |
| 5,868,740 A | 2/1999 | LeVeen et al. |
| 5,868,789 A | 2/1999 | Huebner |
| 5,871,484 A | 2/1999 | Spievack et al. |
| 5,871,486 A | 2/1999 | Huebner et al. |
| 5,871,490 A | 2/1999 | Schulze et al. |
| 5,885,294 A | 3/1999 | Pedlick et al. |
| 5,891,168 A | 4/1999 | Thal |
| 5,893,592 A | 4/1999 | Schulze et al. |
| 5,895,395 A | 4/1999 | Yeung |
| 5,897,564 A | 4/1999 | Schulze et al. |
| 5,897,574 A | 4/1999 | Bonutti |
| 5,899,902 A | 5/1999 | Brown et al. |
| 5,899,938 A | 5/1999 | Sklar et al. |
| 5,908,421 A | 6/1999 | Beger et al. |
| 5,908,436 A | 6/1999 | Cuschieri et al. |
| 5,910,148 A | 6/1999 | Reimels et al. |
| 5,911,721 A | 6/1999 | Nicholson et al. |
| 5,918,604 A | 7/1999 | Whelan |
| 5,921,986 A | 7/1999 | Bonutti |
| 5,925,008 A | 7/1999 | Douglas |
| 5,928,267 A | 7/1999 | Bonutti et al. |
| 5,931,838 A | 8/1999 | Vito |
| 5,931,844 A | 8/1999 | Thompson et al. |
| 5,931,869 A | 8/1999 | Boucher et al. |
| 5,935,149 A | 8/1999 | Ek |
| 5,938,668 A | 8/1999 | Scirica et al. |
| 5,941,439 A | 8/1999 | Kammerer et al. |
| 5,941,900 A | 8/1999 | Bonutti |
| 5,944,739 A | 8/1999 | Zlock et al. |
| 5,946,783 A | 9/1999 | Plociennik et al. |
| 5,947,915 A | 9/1999 | Thibodo, Jr. |
| 5,947,982 A | 9/1999 | Duran |
| 5,948,002 A | 9/1999 | Bonutti |
| 5,951,559 A | 9/1999 | Burkhart |
| 5,951,560 A | 9/1999 | Simon et al. |
| 5,954,747 A | 9/1999 | Clark |
| 5,957,953 A | 9/1999 | DiPoto et al. |
| 5,961,521 A | 10/1999 | Roger et al. |
| 5,961,524 A | 10/1999 | Crombie |
| 5,964,764 A | 10/1999 | West, Jr. et al. |
| 5,964,767 A | 10/1999 | Tapia et al. |
| 5,964,783 A | 10/1999 | Grafton et al. |
| 5,968,045 A | 10/1999 | Frazier |
| 5,968,047 A | 10/1999 | Reed |
| 5,976,125 A | 11/1999 | Graham |
| 5,976,127 A | 11/1999 | Lax |
| 5,980,524 A | 11/1999 | Justin et al. |
| 5,980,558 A | 11/1999 | Wiley |
| 5,980,559 A | 11/1999 | Bonutti |
| 5,989,252 A | 11/1999 | Fumex et al. |
| 5,989,256 A | 11/1999 | Kuslich et al. |
| 5,989,282 A | 11/1999 | Bonutti |
| 5,993,452 A | 11/1999 | Vandewalle |
| 5,997,542 A | 12/1999 | Burke |

| | | |
|---|---|---|
| 5,997,552 A | 12/1999 | Person et al. |
| 6,001,100 A | 12/1999 | Sherman et al. |
| 6,007,567 A | 12/1999 | Bonutti |
| 6,010,525 A | 1/2000 | Bonutti et al. |
| 6,016,727 A | 1/2000 | Morgan |
| 6,022,352 A | 2/2000 | Vandewalle |
| 6,022,373 A | 2/2000 | Li |
| 6,024,758 A | 2/2000 | Thal |
| 6,027,523 A | 2/2000 | Schmieding |
| 6,033,430 A | 3/2000 | Bonutti |
| 6,039,753 A | 3/2000 | Meislin |
| 6,042,601 A | 3/2000 | Smith |
| 6,045,551 A | 4/2000 | Bonutti |
| 6,045,571 A | 4/2000 | Hill et al. |
| 6,045,573 A | 4/2000 | Wenstrom, Jr. et al. |
| 6,045,574 A | 4/2000 | Thal |
| 6,047,826 A | 4/2000 | Kalinski et al. |
| 6,048,343 A | 4/2000 | Mathis et al. |
| 6,051,006 A | 4/2000 | Shluzas et al. |
| 6,053,916 A | 4/2000 | Moore |
| 6,056,752 A | 5/2000 | Roger et al. |
| 6,056,772 A | 5/2000 | Bonutti |
| 6,056,773 A | 5/2000 | Bonutti |
| 6,059,817 A | 5/2000 | Bonutti et al. |
| 6,062,344 A | 5/2000 | Okabe et al. |
| 6,068,648 A | 5/2000 | Cole et al. |
| 6,074,403 A | 6/2000 | Nord |
| 6,077,277 A | 6/2000 | Mollenauer et al. |
| 6,077,292 A | 6/2000 | Bonutti |
| 6,086,591 A | 7/2000 | Bojarski |
| 6,086,592 A | 7/2000 | Rosenberg et al. |
| 6,086,608 A | 7/2000 | Ek et al. |
| 6,096,060 A | 8/2000 | Fitts et al. |
| 6,099,530 A | 8/2000 | Simonian et al. |
| 6,099,568 A | 8/2000 | Simonian et al. |
| 6,106,545 A | 8/2000 | Egan |
| 6,110,128 A | 8/2000 | Andelin et al. |
| 6,117,160 A | 9/2000 | Bonutti |
| 6,117,162 A | 9/2000 | Schmieding et al. |
| 6,123,710 A | 9/2000 | Pinczewski et al. |
| 6,132,433 A | 10/2000 | Whelan |
| 6,132,437 A | 10/2000 | Omurtag et al. |
| 6,139,565 A | 10/2000 | Stone et al. |
| RE36,974 E | 11/2000 | Bonutti |
| 6,143,017 A | 11/2000 | Thal |
| 6,146,406 A | 11/2000 | Shluzas et al. |
| 6,146,408 A | 11/2000 | Bartlett |
| 6,149,653 A | 11/2000 | Deslauriers |
| 6,149,669 A | 11/2000 | Li |
| 6,152,928 A | 11/2000 | Wenstrom, Jr. |
| 6,152,934 A | 11/2000 | Harper et al. |
| 6,152,936 A | 11/2000 | Christy et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,165,203 A | 12/2000 | Krebs |
| 6,168,598 B1 | 1/2001 | Martello |
| 6,168,628 B1 | 1/2001 | Huebner |
| 6,179,840 B1 | 1/2001 | Bowman |
| 6,187,025 B1 | 2/2001 | Machek |
| 6,190,401 B1 | 2/2001 | Green et al. |
| 6,190,411 B1 | 2/2001 | Lo et al. |
| 6,193,754 B1 | 2/2001 | Seedhom et al. |
| 6,200,329 B1 | 3/2001 | Fung et al. |
| 6,200,330 B1 | 3/2001 | Benderev et al. |
| 6,203,565 B1 | 3/2001 | Bonutti et al. |
| 6,203,572 B1 | 3/2001 | Johnson et al. |
| 6,206,883 B1 | 3/2001 | Tunc |
| 6,210,376 B1 | 4/2001 | Grayson |
| 6,214,012 B1 | 4/2001 | Karpman et al. |
| 6,221,107 B1 | 4/2001 | Steiner et al. |
| 6,228,096 B1 | 5/2001 | Marchand |
| 6,231,592 B1 | 5/2001 | Bonutti et al. |
| 6,235,057 B1 | 5/2001 | Roger et al. |
| 6,238,395 B1 | 5/2001 | Bonutti |
| 6,241,734 B1 | 6/2001 | Scribner et al. |
| 6,241,747 B1 | 6/2001 | Ruff |
| 6,241,771 B1 | 6/2001 | Gresser et al. |
| 6,245,081 B1 | 6/2001 | Bowman et al. |
| 6,258,091 B1 | 7/2001 | Sevrain et al. |
| 6,267,766 B1 | 7/2001 | Burkhart |
| 6,269,716 B1 | 8/2001 | Amis |
| 6,270,518 B1 | 8/2001 | Pedlick et al. |
| 6,273,890 B1 | 8/2001 | Frazier |
| 6,283,973 B1 | 9/2001 | Hubbard et al. |
| 6,283,996 B1 | 9/2001 | Chervitz et al. |
| 6,287,325 B1 | 9/2001 | Bonutti |
| 6,293,961 B2 | 9/2001 | Schwartz et al. |
| 6,296,659 B1 | 10/2001 | Foerster |
| 6,299,615 B1 | 10/2001 | Huebner |
| 6,302,888 B1 | 10/2001 | Mellinger et al. |
| 6,306,156 B1 | 10/2001 | Clark |
| 6,306,159 B1 | 10/2001 | Schwartz et al. |
| 6,309,405 B1 | 10/2001 | Bonutti |
| 6,312,448 B1 | 11/2001 | Bonutti |
| 6,319,271 B1 | 11/2001 | Schwartz et al. |
| 6,328,758 B1 | 12/2001 | Tornier et al. |
| 6,342,060 B1 | 1/2002 | Adams |
| 6,343,531 B2 | 2/2002 | Amis |
| 6,364,897 B1 | 4/2002 | Bonutti |
| 6,368,322 B1 | 4/2002 | Luks et al. |
| 6,368,326 B1 | 4/2002 | Dakin et al. |
| 6,368,343 B1 | 4/2002 | Bonutti et al. |
| 6,371,124 B1 | 4/2002 | Whelan |
| 6,379,361 B1 | 4/2002 | Beck, Jr. et al. |
| 6,383,190 B1 | 5/2002 | Preissman |
| 6,383,199 B2 | 5/2002 | Carter et al. |
| 6,387,113 B1 | 5/2002 | Hawkins et al. |
| 6,387,129 B2 | 5/2002 | Rieser et al. |
| 6,398,785 B2 | 6/2002 | Carchidi et al. |
| 6,406,479 B1 | 6/2002 | Justin et al. |
| 6,409,743 B1 | 6/2002 | Fenton, Jr. |
| 6,413,260 B1 | 7/2002 | Berrevoets et al. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,436,124 B1 | 8/2002 | Anderson et al. |
| 6,440,134 B1 | 8/2002 | Zaccherotti et al. |
| 6,440,136 B1 | 8/2002 | Gambale et al. |
| 6,447,516 B1 | 9/2002 | Bonutti |
| 6,451,030 B2 | 9/2002 | Li et al. |
| 6,454,768 B1 | 9/2002 | Jackson |
| 6,458,134 B1 | 10/2002 | Songer et al. |
| 6,461,373 B2 | 10/2002 | Wyman et al. |
| 6,464,713 B2 | 10/2002 | Bonutti |
| 6,468,293 B2 | 10/2002 | Bonutti et al. |
| 6,471,707 B1 | 10/2002 | Miller et al. |
| 6,475,230 B1 | 11/2002 | Bonutti et al. |
| 6,482,210 B1 | 11/2002 | Skiba et al. |
| 6,485,504 B1 | 11/2002 | Johnson et al. |
| 6,497,901 B1 | 12/2002 | Royer |
| 6,500,184 B1 | 12/2002 | Chan et al. |
| 6,500,195 B2 | 12/2002 | Bonutti |
| RE37,963 E | 1/2003 | Thal |
| 6,503,267 B2 | 1/2003 | Bonutti et al. |
| 6,508,820 B2 | 1/2003 | Bales |
| 6,508,821 B1 | 1/2003 | Schwartz et al. |
| 6,508,830 B2 | 1/2003 | Steiner |
| 6,511,498 B1 | 1/2003 | Fumex et al. |
| 6,511,499 B2 | 1/2003 | Schmieding et al. |
| 6,517,542 B1 | 2/2003 | Papay et al. |
| 6,517,552 B1 | 2/2003 | Nord et al. |
| 6,517,578 B2 | 2/2003 | Hein et al. |
| 6,517,579 B1 | 2/2003 | Paulos et al. |
| 6,520,964 B2 | 2/2003 | Tallarida et al. |
| 6,520,980 B1 | 2/2003 | Foerster |
| 6,524,317 B1 | 2/2003 | Ritchart et al. |
| 6,527,777 B2 | 3/2003 | Justin |
| 6,527,794 B1 | 3/2003 | McDevitt et al. |
| 6,527,795 B1 | 3/2003 | Lizardi |
| 6,533,795 B1 | 3/2003 | Tran et al. |
| 6,533,802 B2 | 3/2003 | Bojarski et al. |
| 6,537,319 B2 | 3/2003 | Whelan |
| 6,540,750 B2 | 4/2003 | Burkhart |
| 6,540,770 B1 | 4/2003 | Tornier et al. |
| 6,544,281 B2 | 4/2003 | ElAttrache et al. |
| 6,547,564 B1 | 4/2003 | Hansson et al. |

| Patent | Date | Inventor |
|---|---|---|
| 6,547,800 B2 | 4/2003 | Foerster et al. |
| 6,551,330 B1 | 4/2003 | Bain et al. |
| 6,551,343 B1 | 4/2003 | Tormala et al. |
| 6,553,802 B1 | 4/2003 | Jacob et al. |
| 6,554,830 B1 | 4/2003 | Chappius |
| 6,554,852 B1 | 4/2003 | Oberlander |
| 6,554,862 B2 | 4/2003 | Hays et al. |
| 6,562,071 B2 | 5/2003 | Jarvinen et al. |
| 6,565,572 B2 | 5/2003 | Chappius |
| 6,565,573 B1 | 5/2003 | Ferrante et al. |
| 6,569,186 B1 | 5/2003 | Winters et al. |
| 6,569,187 B1 | 5/2003 | Bonutti et al. |
| 6,572,635 B1 | 6/2003 | Bonutti |
| 6,575,925 B1 | 6/2003 | Noble |
| 6,579,295 B1 | 6/2003 | Supinski |
| 6,582,453 B1 | 6/2003 | Tran et al. |
| 6,585,730 B1 | 7/2003 | Foerster |
| 6,585,740 B2 | 7/2003 | Schlapfer et al. |
| 6,585,750 B2 | 7/2003 | Bonutti et al. |
| 6,589,245 B1 | 7/2003 | Weiler et al. |
| 6,589,246 B1 | 7/2003 | Hack et al. |
| 6,592,609 B1 | 7/2003 | Bonutti |
| 6,595,911 B2 | 7/2003 | LoVuolo |
| 6,599,289 B1 | 7/2003 | Bojarski et al. |
| 6,605,096 B1 | 8/2003 | Ritchart |
| 6,607,548 B2 | 8/2003 | Pohjonen et al. |
| 6,613,018 B2 | 9/2003 | Bagga et al. |
| 6,616,694 B1 | 9/2003 | Hart |
| 6,620,166 B1 | 9/2003 | Wenstrom, Jr. et al. |
| 6,620,185 B1 | 9/2003 | Harvie et al. |
| 6,620,195 B2 | 9/2003 | Goble et al. |
| 6,620,329 B2 | 9/2003 | Rosen et al. |
| 6,620,349 B1 | 9/2003 | Lopez |
| 6,623,492 B1 | 9/2003 | Berube et al. |
| 6,623,524 B2 | 9/2003 | Schmieding |
| 6,626,910 B1 | 9/2003 | Hugues et al. |
| 6,626,919 B1 | 9/2003 | Swanstrom |
| 6,629,977 B1 | 10/2003 | Wolf |
| 6,635,073 B2 | 10/2003 | Bonutti |
| 6,638,279 B2 | 10/2003 | Bonutti |
| 6,641,596 B1 | 11/2003 | Lizardi |
| 6,641,597 B2 | 11/2003 | Burkhart et al. |
| 6,645,227 B2 | 11/2003 | Fallin et al. |
| 6,652,562 B2 | 11/2003 | Collier et al. |
| 6,652,563 B2 | 11/2003 | Dreyfuss |
| 6,656,182 B1 | 12/2003 | Hayhurst |
| 6,656,183 B2 | 12/2003 | Colleran et al. |
| 6,658,182 B1 | 12/2003 | Gonthier et al. |
| 6,660,008 B1 | 12/2003 | Foerster et al. |
| 6,660,022 B1 | 12/2003 | Li et al. |
| 6,663,634 B2 | 12/2003 | Ahrens et al. |
| 6,663,656 B2 | 12/2003 | Schmieding et al. |
| 6,666,868 B2 | 12/2003 | Fallin |
| 6,682,549 B2 | 1/2004 | Bartlett |
| 6,685,728 B2 | 2/2004 | Sinnott et al. |
| 6,689,137 B2 | 2/2004 | Reed |
| 6,689,154 B2 | 2/2004 | Bartlett |
| 6,692,499 B2 | 2/2004 | Tormala et al. |
| 6,712,849 B2 | 3/2004 | Re et al. |
| 6,716,224 B2 | 4/2004 | Singhatat |
| 6,716,957 B2 | 4/2004 | Tunc |
| 6,730,092 B2 | 5/2004 | Songer |
| 6,730,124 B2 | 5/2004 | Steiner |
| 6,736,799 B1 | 5/2004 | Erbe et al. |
| 6,746,483 B1 | 6/2004 | Bojarski et al. |
| 6,755,836 B1 | 6/2004 | Lewis |
| 6,761,739 B2 | 7/2004 | Shepard |
| 6,767,037 B2 | 7/2004 | Wenstrom, Jr. |
| 6,770,076 B2 | 8/2004 | Foerster |
| 6,770,084 B1 | 8/2004 | Bain et al. |
| 6,773,450 B2 | 8/2004 | Leung et al. |
| 6,780,190 B2 | 8/2004 | Maroney |
| 6,780,198 B1 | 8/2004 | Gregoire et al. |
| 6,802,862 B1 | 10/2004 | Roger et al. |
| 6,808,502 B2 | 10/2004 | Nguyen et al. |
| 6,808,526 B1 | 10/2004 | Magerl et al. |
| 6,814,741 B2 | 11/2004 | Bowman et al. |
| 6,830,572 B2 | 12/2004 | McDevitt et al. |
| 6,833,005 B1 | 12/2004 | Mantas et al. |
| 6,840,953 B2 | 1/2005 | Martinek |
| 6,860,885 B2 | 3/2005 | Bonutti |
| 6,863,671 B1 | 3/2005 | Strobel et al. |
| 6,872,040 B2 | 3/2005 | Deeg et al. |
| 6,875,216 B2 | 4/2005 | Wolf |
| 6,884,249 B2 | 4/2005 | May et al. |
| 6,887,259 B2 | 5/2005 | Lizardi |
| 6,890,354 B2 | 5/2005 | Steiner et al. |
| 6,893,448 B2 | 5/2005 | O'Quinn et al. |
| 6,896,686 B2 | 5/2005 | Weber |
| 6,899,722 B2 | 5/2005 | Bonutti |
| 6,902,573 B2 | 6/2005 | Strobel et al. |
| 6,908,466 B1 | 6/2005 | Bonutti et al. |
| 6,916,292 B2 | 7/2005 | Morawski et al. |
| 6,916,321 B2 | 7/2005 | TenHuisen et al. |
| 6,921,402 B2 | 7/2005 | Contiliano et al. |
| 6,923,823 B1 | 8/2005 | Bartlett et al. |
| 6,923,824 B2 | 8/2005 | Morgan et al. |
| 6,951,565 B2 | 10/2005 | Keane et al. |
| 6,972,027 B2 | 12/2005 | Fallin et al. |
| 6,980,903 B2 | 12/2005 | Daniels et al. |
| 6,986,781 B2 | 1/2006 | Smith |
| 6,989,034 B2 | 1/2006 | Hammer et al. |
| 7,066,942 B2 | 6/2006 | Treace |
| 7,066,944 B2 | 6/2006 | Laufer et al. |
| 7,105,010 B2 | 9/2006 | Hart et al. |
| 7,112,221 B2 | 9/2006 | Harris et al. |
| 7,118,583 B2 | 10/2006 | O'Quinn et al. |
| 7,137,996 B2 | 11/2006 | Steiner et al. |
| 7,141,066 B2 | 11/2006 | Steiner et al. |
| 7,153,307 B2 | 12/2006 | Scribner et al. |
| 7,153,312 B1 | 12/2006 | Torrie et al. |
| 7,201,722 B2 | 4/2007 | Krueger |
| 7,261,716 B2 | 8/2007 | Strobel et al. |
| 7,264,634 B2 | 9/2007 | Schmieding |
| 7,285,124 B2 | 10/2007 | Foerster |
| 7,306,417 B2 | 12/2007 | Dorstewitz |
| 7,390,332 B2 | 6/2008 | Selvitelli et al. |
| 7,601,165 B2 | 10/2009 | Stone |
| 7,608,098 B1 | 10/2009 | Stone et al. |
| 7,615,076 B2 | 11/2009 | Cauthen, III et al. |
| 7,651,509 B2 | 1/2010 | Bojarski et al. |
| 7,658,751 B2 | 2/2010 | Stone et al. |
| 7,678,123 B2 | 3/2010 | Chanduszko |
| 7,695,493 B2 | 4/2010 | Saadat et al. |
| 7,736,379 B2 | 6/2010 | Ewers et al. |
| 7,758,594 B2 | 7/2010 | Lamson et al. |
| 2001/0014825 A1 | 8/2001 | Burke et al. |
| 2001/0037131 A1 | 11/2001 | Schmieding et al. |
| 2001/0037153 A1 | 11/2001 | Rockwood et al. |
| 2001/0041916 A1 | 11/2001 | Bonutti |
| 2001/0041937 A1 | 11/2001 | Rieser et al. |
| 2001/0041938 A1 | 11/2001 | Hein |
| 2001/0044639 A1 | 11/2001 | Levinson |
| 2001/0047206 A1 | 11/2001 | Sklar et al. |
| 2001/0051816 A1 | 12/2001 | Enzerink et al. |
| 2001/0053934 A1 | 12/2001 | Schmieding |
| 2002/0001964 A1 | 1/2002 | Choi |
| 2002/0004669 A1 | 1/2002 | Bartlett |
| 2002/0007182 A1 | 1/2002 | Kim |
| 2002/0010513 A1 | 1/2002 | Schmieding |
| 2002/0013608 A1 | 1/2002 | ElAttrache et al. |
| 2002/0019649 A1 | 2/2002 | Sikora et al. |
| 2002/0055780 A1 | 5/2002 | Sklar |
| 2002/0058966 A1 | 5/2002 | Tormala et al. |
| 2002/0099411 A1 | 7/2002 | Bartlett |
| 2002/0111653 A1 | 8/2002 | Foerster |
| 2002/0120270 A1 | 8/2002 | Trieu et al. |
| 2002/0120292 A1 | 8/2002 | Morgan |
| 2002/0123752 A1 | 9/2002 | Schultheiss et al. |
| 2002/0128684 A1 | 9/2002 | Foerster |
| 2002/0147463 A1 | 10/2002 | Martinek |
| 2002/0161401 A1 | 10/2002 | Steiner |
| 2002/0161439 A1 | 10/2002 | Strobel et al. |
| 2002/0169452 A1 | 11/2002 | Tormala et al. |
| 2002/0169477 A1 | 11/2002 | Demopulos et al. |
| 2002/0169478 A1 | 11/2002 | Schwartz et al. |
| 2002/0173788 A1 | 11/2002 | Bojarski et al. |
| 2002/0188298 A1 | 12/2002 | Chan |

| | | |
|---|---|---|
| 2003/0023268 A1 | 1/2003 | Lizardi |
| 2003/0032961 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0065391 A1 | 4/2003 | Re et al. |
| 2003/0078603 A1 | 4/2003 | Schaller et al. |
| 2003/0078617 A1 | 4/2003 | Schwartz et al. |
| 2003/0083662 A1 | 5/2003 | Middleton |
| 2003/0088251 A1 | 5/2003 | Braun et al. |
| 2003/0088272 A1 | 5/2003 | Smith |
| 2003/0105477 A1 | 6/2003 | Schwartz et al. |
| 2003/0120309 A1 | 6/2003 | Colleran et al. |
| 2003/0130694 A1 | 7/2003 | Bojarski et al. |
| 2003/0135214 A1 | 7/2003 | Fetto et al. |
| 2003/0135239 A1 | 7/2003 | Gabriel et al. |
| 2003/0135963 A1 | 7/2003 | Holbrook et al. |
| 2003/0152522 A1 | 8/2003 | Miller et al. |
| 2003/0167072 A1 | 9/2003 | Oberlander |
| 2003/0167090 A1 | 9/2003 | Chervitz et al. |
| 2003/0171811 A1 | 9/2003 | Steiner et al. |
| 2003/0176865 A1 | 9/2003 | Supinski |
| 2003/0176919 A1 | 9/2003 | Schmieding |
| 2003/0181925 A1 | 9/2003 | Bain et al. |
| 2003/0195528 A1 | 10/2003 | Ritchart |
| 2003/0220660 A1 | 11/2003 | Kortenbach et al. |
| 2003/0225459 A1 | 12/2003 | Hammer et al. |
| 2004/0002734 A1 | 1/2004 | Fallin et al. |
| 2004/0006345 A1 | 1/2004 | Vlahos et al. |
| 2004/0006346 A1 | 1/2004 | Holmen et al. |
| 2004/0015171 A1 | 1/2004 | Bojarski et al. |
| 2004/0015172 A1 | 1/2004 | Biedermann et al. |
| 2004/0024456 A1 | 2/2004 | Brown et al. |
| 2004/0087981 A1 | 5/2004 | Berube et al. |
| 2004/0092936 A1 | 5/2004 | Miller et al. |
| 2004/0098051 A1 | 5/2004 | Fallin et al. |
| 2004/0111117 A1 | 6/2004 | Colleran et al. |
| 2004/0122431 A1 | 6/2004 | Biedermann et al. |
| 2004/0133211 A1 | 7/2004 | Raskin et al. |
| 2004/0138664 A1 | 7/2004 | Bowman |
| 2004/0138683 A1 | 7/2004 | Shelton et al. |
| 2004/0138704 A1 | 7/2004 | Gambale et al. |
| 2004/0138706 A1 | 7/2004 | Abrams et al. |
| 2004/0143344 A1 | 7/2004 | Malaviya et al. |
| 2004/0153103 A1 | 8/2004 | Schwartz et al. |
| 2004/0153153 A1 | 8/2004 | Elson et al. |
| 2004/0162579 A1 | 8/2004 | Foerster |
| 2004/0166169 A1 | 8/2004 | Malaviya et al. |
| 2004/0182968 A1 | 9/2004 | Gentry |
| 2004/0220574 A1 | 11/2004 | Pelo et al. |
| 2004/0225292 A1 | 11/2004 | Sasso et al. |
| 2004/0236353 A1 | 11/2004 | Bain et al. |
| 2004/0243139 A1 | 12/2004 | Lewis et al. |
| 2004/0243178 A1 | 12/2004 | Haut et al. |
| 2004/0249394 A1 | 12/2004 | Morris et al. |
| 2004/0267164 A1 | 12/2004 | Rhodes et al. |
| 2004/0267265 A1 | 12/2004 | Kyle |
| 2004/0267270 A1 | 12/2004 | Jacobs et al. |
| 2004/0267276 A1 | 12/2004 | Camino et al. |
| 2004/0267277 A1 | 12/2004 | Zannis et al. |
| 2004/0267304 A1 | 12/2004 | Zannis et al. |
| 2005/0027307 A1 | 2/2005 | Schwartz et al. |
| 2005/0033363 A1 | 2/2005 | Bojarski et al. |
| 2005/0038426 A1 | 2/2005 | Chan |
| 2005/0055027 A1 | 3/2005 | Yeung et al. |
| 2005/0064042 A1 | 3/2005 | Vunjak-Novakovic et al. |
| 2005/0074495 A1 | 4/2005 | Schwartz et al. |
| 2005/0090828 A1 | 4/2005 | Alford |
| 2005/0096696 A1 | 5/2005 | Forsberg |
| 2005/0096697 A1 | 5/2005 | Forsberg et al. |
| 2005/0107828 A1 | 5/2005 | Reese |
| 2005/0119531 A1 | 6/2005 | Sharratt |
| 2005/0125073 A1 | 6/2005 | Orban et al. |
| 2005/0137600 A1 | 6/2005 | Jacobs et al. |
| 2005/0149033 A1 | 7/2005 | McGuire et al. |
| 2005/0159812 A1 | 7/2005 | Dinger et al. |
| 2005/0165416 A1 | 7/2005 | Bojarski et al. |
| 2005/0165482 A1 | 7/2005 | Goldhahn et al. |
| 2005/0203620 A1 | 9/2005 | Steiner et al. |
| 2005/0222618 A1 | 10/2005 | Dreyfuss et al. |
| 2005/0222619 A1 | 10/2005 | Dreyfuss et al. |
| 2005/0228448 A1 | 10/2005 | Li |
| 2005/0267479 A1* | 12/2005 | Morgan et al. .................. 606/73 |
| 2005/0277961 A1 | 12/2005 | Stone et al. |
| 2005/0283040 A1 | 12/2005 | Greenhalgh |
| 2005/0283156 A1 | 12/2005 | Schmieding et al. |
| 2005/0283158 A1 | 12/2005 | West |
| 2005/0283192 A1 | 12/2005 | Torrie et al. |
| 2006/0030948 A1 | 2/2006 | Manrique et al. |
| 2006/0036265 A1 | 2/2006 | Dant |
| 2006/0064126 A1 | 3/2006 | Fallin et al. |
| 2006/0069334 A1 | 3/2006 | Moskowitz |
| 2006/0084943 A1 | 4/2006 | Rosenman et al. |
| 2006/0100627 A1 | 5/2006 | Stone et al. |
| 2006/0121084 A1 | 6/2006 | Borden et al. |
| 2006/0135958 A1 | 6/2006 | Marissen et al. |
| 2006/0167482 A1 | 7/2006 | Swain et al. |
| 2006/0178680 A1 | 8/2006 | Nelson et al. |
| 2006/0189993 A1 | 8/2006 | Stone |
| 2006/0190042 A1 | 8/2006 | Stone et al. |
| 2006/0229671 A1 | 10/2006 | Steiner et al. |
| 2006/0247642 A1 | 11/2006 | Stone et al. |
| 2006/0271192 A1 | 11/2006 | Olsen et al. |
| 2006/0280768 A1 | 12/2006 | Hwang et al. |
| 2006/0282085 A1 | 12/2006 | Stone et al. |
| 2006/0293709 A1* | 12/2006 | Bojarski et al. ................ 606/232 |
| 2007/0016305 A1 | 1/2007 | Chudik |
| 2007/0055255 A1 | 3/2007 | Siegel |
| 2007/0060922 A1 | 3/2007 | Dreyfuss |
| 2007/0067025 A1 | 3/2007 | Schwartz |
| 2007/0073307 A1 | 3/2007 | Scribner et al. |
| 2007/0078435 A1 | 4/2007 | Stone et al. |
| 2007/0083236 A1 | 4/2007 | Sikora et al. |
| 2007/0093847 A1 | 4/2007 | Scribner et al. |
| 2007/0142838 A1 | 6/2007 | Jordan |
| 2007/0185532 A1 | 8/2007 | Stone et al. |
| 2007/0239209 A1 | 10/2007 | Fallman |
| 2008/0027446 A1 | 1/2008 | Stone et al. |
| 2008/0065114 A1 | 3/2008 | Stone et al. |
| 2008/0082127 A1 | 4/2008 | Stone et al. |
| 2008/0082128 A1 | 4/2008 | Stone |
| 2008/0132932 A1 | 6/2008 | Hoeppner et al. |
| 2008/0140092 A1 | 6/2008 | Stone et al. |
| 2008/0140093 A1 | 6/2008 | Stone et al. |
| 2008/0161852 A1 | 7/2008 | Kaiser et al. |
| 2008/0255613 A1 | 10/2008 | Kaiser et al. |
| 2008/0268064 A1 | 10/2008 | Woodell-May |
| 2008/0269674 A1 | 10/2008 | Stone |
| 2008/0312689 A1 | 12/2008 | Denham et al. |
| 2009/0054928 A1 | 2/2009 | Denham et al. |
| 2009/0062854 A1 | 3/2009 | Kaiser et al. |
| 2009/0082805 A1 | 3/2009 | Kaiser et al. |
| 2009/0192468 A1 | 7/2009 | Stone |
| 2009/0306711 A1 | 12/2009 | Stone et al. |
| 2009/0312776 A1 | 12/2009 | Kaiser et al. |
| 2009/0318961 A1 | 12/2009 | Stone et al. |
| 2010/0042114 A1 | 2/2010 | Schaffhausen |
| 2010/0145384 A1 | 6/2010 | Stone et al. |

FOREIGN PATENT DOCUMENTS

| | | |
|---|---|---|
| AU | 440266 | 10/1967 |
| AU | 2223767 | 11/1968 |
| AU | 5028569 | 8/1970 |
| AU | 5850469 | 1/1971 |
| AU | 5963869 | 2/1971 |
| AU | 1505470 | 11/1971 |
| AU | 3615171 | 5/1973 |
| AU | 7110887 | 10/1987 |
| AU | 639410 | 11/1989 |
| AU | 651929 | 8/1994 |
| DE | 2529669 | 3/1976 |
| DE | 2747312 | 4/1979 |
| DE | 2818254 | 10/1979 |
| DE | 2919009 | 11/1979 |
| DE | 3027138 | 12/1981 |
| DE | 3225620 | 2/1983 |
| DE | 3136083 | 3/1983 |

| | | |
|---|---|---|
| DE | 233303 | 2/1986 |
| DE | 4127550 | 2/1993 |
| DE | 4302397 | 7/1993 |
| DE | 29621340 | 5/1998 |
| DE | 19841252 | 3/2000 |
| EP | 0108912 | 5/1984 |
| EP | 0129442 | 12/1984 |
| EP | 0172130 | 2/1986 |
| EP | 0241240 | 10/1987 |
| EP | 0241792 | 10/1987 |
| EP | 0260970 | 3/1988 |
| EP | 0270704 | 6/1988 |
| EP | 0282789 | 9/1988 |
| EP | 0315371 | 5/1989 |
| EP | 0317406 | 5/1989 |
| EP | 0340159 | 11/1989 |
| EP | 0346183 | 12/1989 |
| EP | 0349173 | 1/1990 |
| EP | 0374088 | 6/1990 |
| EP | 0409364 | 1/1991 |
| EP | 0415915 | 3/1991 |
| EP | 0440991 | 8/1991 |
| EP | 0441065 | 8/1991 |
| EP | 0451932 | 10/1991 |
| EP | 0464480 | 1/1992 |
| EP | 0497079 | 8/1992 |
| EP | 0502509 | 9/1992 |
| EP | 0502698 | 9/1992 |
| EP | 520177 | 12/1992 |
| EP | 0546726 | 6/1993 |
| EP | 0574707 | 12/1993 |
| EP | 0582514 | 2/1994 |
| EP | 0591991 | 4/1994 |
| EP | 0598219 | 5/1994 |
| EP | 0627203 | 12/1994 |
| EP | 0651979 | 5/1995 |
| EP | 0669110 | 8/1995 |
| EP | 0686373 | 12/1995 |
| EP | 0702933 | 3/1996 |
| EP | 0775473 | 5/1997 |
| EP | 0913123 | 5/1999 |
| EP | 0913131 | 5/1999 |
| EP | 99121106 | 10/1999 |
| EP | 991210527 | 10/1999 |
| EP | 0995409 | 4/2000 |
| EP | 1013229 | 6/2000 |
| EP | 1093773 | 4/2001 |
| EP | 1093774 | 4/2001 |
| EP | 1555945 | 7/2005 |
| FR | 2622790 | 5/1989 |
| FR | 2655840 | 6/1991 |
| FR | 2682867 | 4/1993 |
| FR | 2687911 | 9/1993 |
| FR | 2688689 | 9/1993 |
| FR | 2704140 | 10/1994 |
| FR | 2717070 | 9/1995 |
| FR | 2723528 | 2/1996 |
| FR | 2744010 | 8/1997 |
| FR | 2745999 | 9/1997 |
| FR | 2770764 | 5/1999 |
| GB | 401677 | 11/1933 |
| GB | 1413477 | 11/1975 |
| GB | 1485681 | 9/1977 |
| GB | 2083751 | 3/1982 |
| GB | 2118474 | 11/1983 |
| GB | 2227175 | 7/1990 |
| GB | 2253147 | 9/1992 |
| GB | 2312376 | 10/1997 |
| JP | 5362911 | 5/1978 |
| JP | 5362912 | 5/1978 |
| JP | 5374942 | 6/1978 |
| JP | 5378230 | 6/1978 |
| JP | 62159647 | 7/1987 |
| JP | 62295657 | 12/1987 |
| JP | 5269160 | 10/1993 |
| JP | 5300917 | 11/1993 |
| JP | 751292 | 2/1995 |
| JP | 10211213 | 8/1998 |
| WO | WO-8300615 | 3/1983 |
| WO | WO-8603666 | 7/1986 |
| WO | WO-8701270 | 3/1987 |
| WO | WO-8901767 | 3/1989 |
| WO | WO-8909030 | 10/1989 |
| WO | WO-8910096 | 11/1989 |
| WO | WO-9008510 | 8/1990 |
| WO | WO-9203980 | 3/1992 |
| WO | WO-9314705 | 8/1993 |
| WO | WO-9315694 | 8/1993 |
| WO | WO-9502373 | 1/1995 |
| WO | WO-9529637 | 11/1995 |
| WO | WO-9532670 | 12/1995 |
| WO | WO-9629029 | 9/1996 |
| WO | WO-9737603 | 10/1997 |
| WO | WO-9812991 | 4/1998 |
| WO | WO-9812992 | 4/1998 |
| WO | WO-9822047 | 5/1998 |
| WO | WO-9822048 | 5/1998 |
| WO | WO-9901084 | 1/1999 |
| WO | WO-9912480 | 3/1999 |
| WO | WO-9944544 | 9/1999 |
| WO | WO-0040159 | 7/2000 |
| WO | WO-0139671 | 6/2001 |
| WO | WO-0236020 | 5/2002 |
| WO | WO-03071962 | 9/2003 |
| WO | WO-03077772 | 9/2003 |
| WO | WO-2005104992 | 11/2005 |

OTHER PUBLICATIONS

"Technique for ACL Reconstruction with Acufex Director Drill Guide and Endobutton CL," by Thomas D. Roseberg, copyright 1999 Smith & Nephew.

A. Weiler, et al; Biodegradierbare Interferenzschrauben in der Kreuzbandchirurgie; OP-JOURNAL 14 pp. 278-284; 1998.

Arthrotek, A Biomet Company; Knees; Sure fire Hybrid Meniscal Device.

Arthrotek, A Biomet Company; Sure fire Hybrid Meniscal Device; Launch Date: Fall AANA 2004.

Bio-Intrafix (TCP/PLA & Intrafix, Tibial Soft Tissue Fasteners, by DePuy Mitek, 6 sheets, (date unknown).

F. Alan Barber, M.D., "Uses and Abuses of Sutures and Anchors," Shoulder Scope, San Diego Shoulder Arthroscopy Library.

F. Alan Barber, M.D., "Using Sutures and Anchors," San Diego Shoulder Arthroscopy Course, 17th Annual Meeting.

Flavia Namie Azato, et al. "Traction endurance biomechanical study of metallic suture anchors at different insertion angles," Acta ortop. bras., vol. 11, No. 1, Sao Paulo, Jan./Mar. 2003.

Hecker AT, et al., "Pull-out strength of suture anchors for rotator cuff and Bankart lesion repairs," Am J Sports Med. 1993.

Lawhorn, M.D., Keith, MaxFire™ Meniscal Repair Device with Zip Loop™ Technology, Biomet Sports Medicine, Feb. 29, 2008.

Mark D. Miller et al.; "Pitfalls Associated with FasT-Fix Meniscal Repair," Arthroscopy: The Journal of Arthroscopic and Related Surgery, vol. 18, No. 8 Oct. 2002: pp. 939-943.

Opus Medical; The AutoCuff System; www.opusmedical.com; 2003.

Patrick Hunt, et al.; Development of a Perforated Biodegradable Interference Screw; Arthroscopy: The Journal of Arthroscopic and Related Surgery, vol. 21, No. 3; pp. 258-265; Mar. 2005.

Roy Alan Majors, M.D.; "Meniscal repairs: proven techniques and current trends," Lippincott Williams & Wilkins, Inc.; 2002.

Shoulder Arthroscopy; pp. H-2-H-22.

Smith & Nephew Endoscopy, "Endoscopic Meniscal Repair Using the T-Fix;" 1996.

Smith & Nephew, "Fast-Fix," Meniscal Repair System; 2001.

Stuart E. Fromm, M.D., RapidLoc, Meniscal Repair System, Mitek Products, Ethicon, 2001.

ToggleLoc™ Femoral Fixation Device, Arthrotek, Mar. 31, 2006.

"Do your next distal tendon repair with . . . The Lubbers Technique", Teno Fix® brochure, 2003 (2 pages) Ortheon® Medical.

"Make your next tendon repair an open-and-shut case. The Teno Fix® Tendon Repair System", Teno Fix® brochure, 2003 (2 pages) Ortheon® Medical.

US 6,238,418, 05/2001, Schwartz et al. (withdrawn)

* cited by examiner

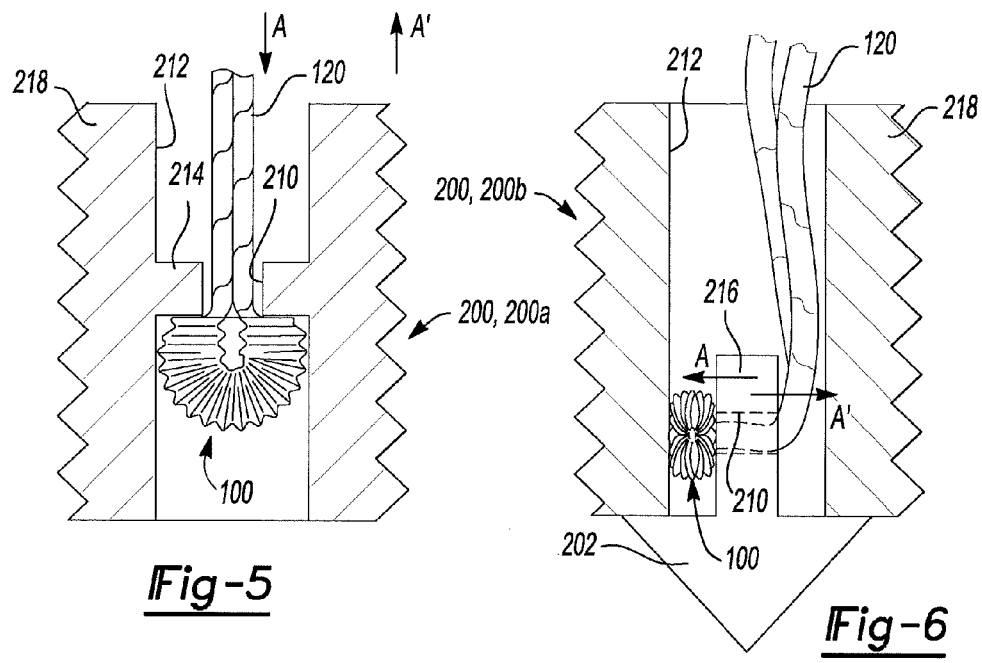
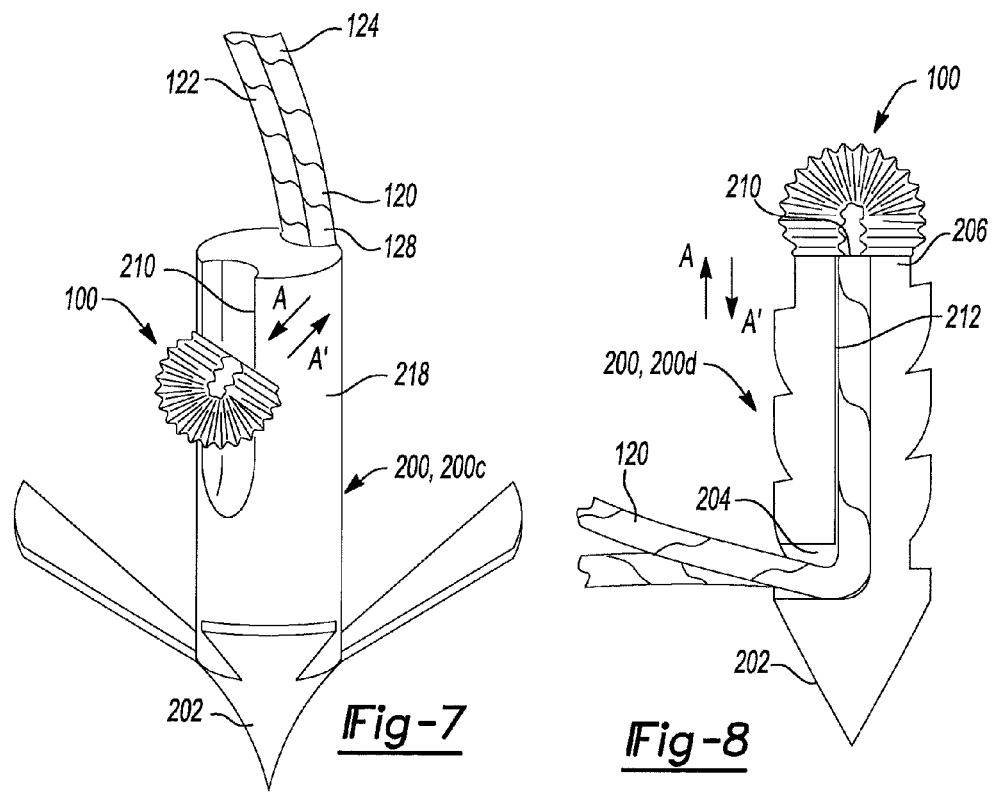

METHOD FOR TISSUE FIXATION

CROSS-REFERENCE TO RELATED APPLICATIONS

This application is a continuation-in-part of U.S. patent application Ser. No. 11/347,661, now U.S. Pat. No. 7,749, 250, filed on Feb. 3, 2006. The disclosure of the above application is incorporated herein by reference.

INTRODUCTION

Trauma or disease in soft tissue, such as cartilage, ligament, or muscle can cause tears or detachment from bone or other defects that can be repaired by reattaching or securing the soft tissue to the bone. Various devices and methods are known for attaching and securing soft tissue to bone.

The present teachings provide a versatile tissue fixation method that can be used with various bone anchors or other implantable fixation members to attach soft tissue to bone or any tissue to other tissue.

SUMMARY

The present teachings provide a method for securing a strand to at least one fixation member for a surgical procedure, wherein the fixation member includes an aperture therethrough. The method includes passing a strand having first and second ends through a flexible sleeve, passing the sleeve through the aperture of the fixation member in a first direction, tensioning the strand, and moving the sleeve in a second direction different than the first direction to secure the sleeve to the fixation member without tying the strand on the fixation member.

The present teachings provide a method for securing a strand to a plurality of anchors for a surgical procedure. The method includes inserting a plurality of anchors into the bone, passing a flexible strand having first and second ends through a plurality of flexible sleeves serially coupled on the strand, passing each sleeve in a first configuration into and through an aperture of a corresponding anchor in a first direction, deforming each sleeve to a second configuration, and tying a single knot at the first and second ends of the strand.

The present teachings provide a method for securing a strand to a plurality of bone anchors for a surgical procedure. The method includes passing a flexible strand slidably through a plurality of flexible sleeves, forming a single slipknot on a portion of the strand outside all the sleeves, the slipknot the defining a closed loop, knotlessly securing each sleeve into a corresponding bone anchor, and reducing a length of the loop.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 5 is a side view of the connector device of FIG. 1, shown with a first anchor;

FIG. 6 is a side view of the connector device of FIG. 1, shown with a second anchor;

FIG. 7 is a side view of the connector device of FIG. 1, shown with a third anchor;

FIG. 8 is a side view of the connector device of FIG. 1, shown with a fourth anchor.

DESCRIPTION OF VARIOUS ASPECTS

The following description is merely exemplary in nature and is in no way intended to limit the scope of the present teachings, applications, or uses. The present teachings can be used for various orthopedic applications including soft tissue repair, and generally attaching soft tissue to bone, or attaching suture or other anchors to bone, or any other tissue repair procedure. The present teachings can also be used for repairing any fibrous tissue, such as muscle, ligament or tendon in an arthroscopic or other open procedure, including rotator cuff reconstruction, acromioclavicular (AC) reconstruction, anterior cruciate ligament reconstruction (ACL) and generally for fastening tendons, grafts, or strands to fibrous tissue and bone. Additionally, the present teachings can be used for repairing tissue in cardiological, laparoscopic, urological, plastic or other procedures.

Figure 1:
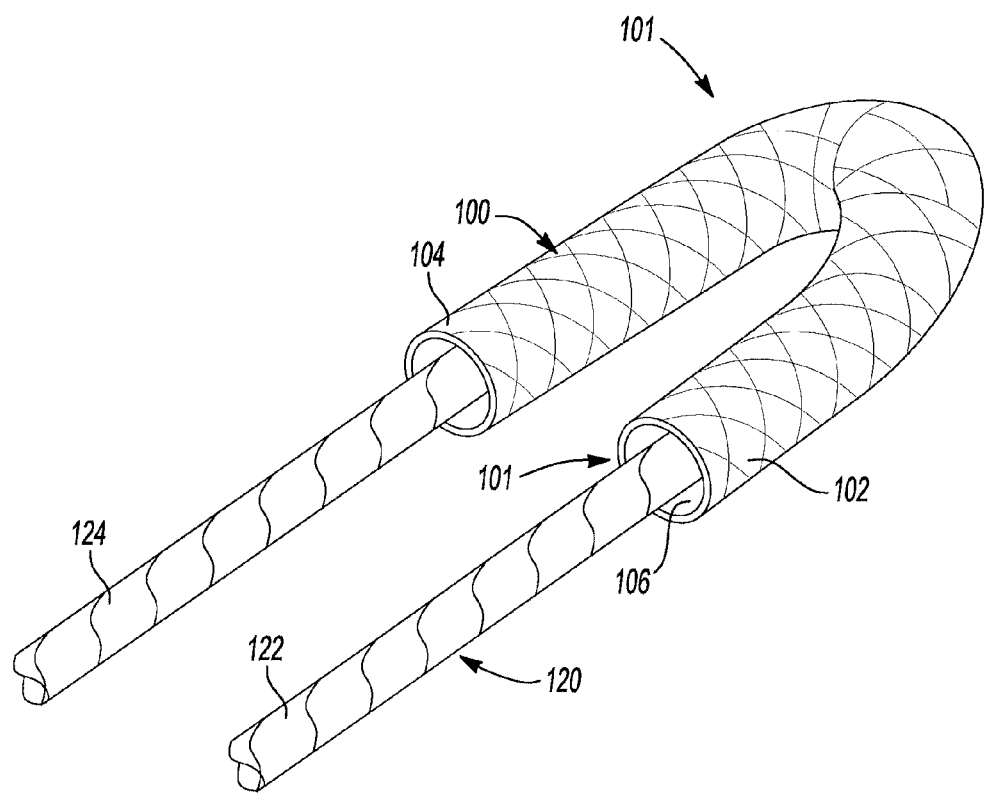
FIG. 1 is a perspective view of a connector device according to the present teachings.

Referring to FIG. 1, an exemplary connector device 101 that can be used for attaching soft tissue to bone is illustrated. The connector device 101 can include a flexible tubular sleeve 100 having an inner bore 106 that extends between first and second open ends 102, 104. The sleeve 100 can be made of resorbable or non-resorbable materials, including braided suture, sponges and sponge-like, perforated materials, woven/braided from biocompatible materials or fibers, such as, for example, polymer, polyester, polyethylene, cotton, silk, or other natural or synthetic materials. The sleeve 100 can be made of suture material braided from thin filaments into a form that does not include a core filament. The sleeve 100 can have a generally flaccid shape that can be manipulated in different configurations like a piece of string or shoelace, for example. Accordingly, the sleeve 100 can be bent, folded or otherwise manipulated or deformed into various configurations, such as a bent or U-shape configuration shown in FIGS. 1, 1A and 1B, or a substantially straight configuration shown in FIG. 4, or a deformed or bunched-up, puckered configuration, such as the ball-like configuration shown in FIG. 3, or the bell-like shaped shown in FIG. 3A, as discussed below.

Figure 1A:
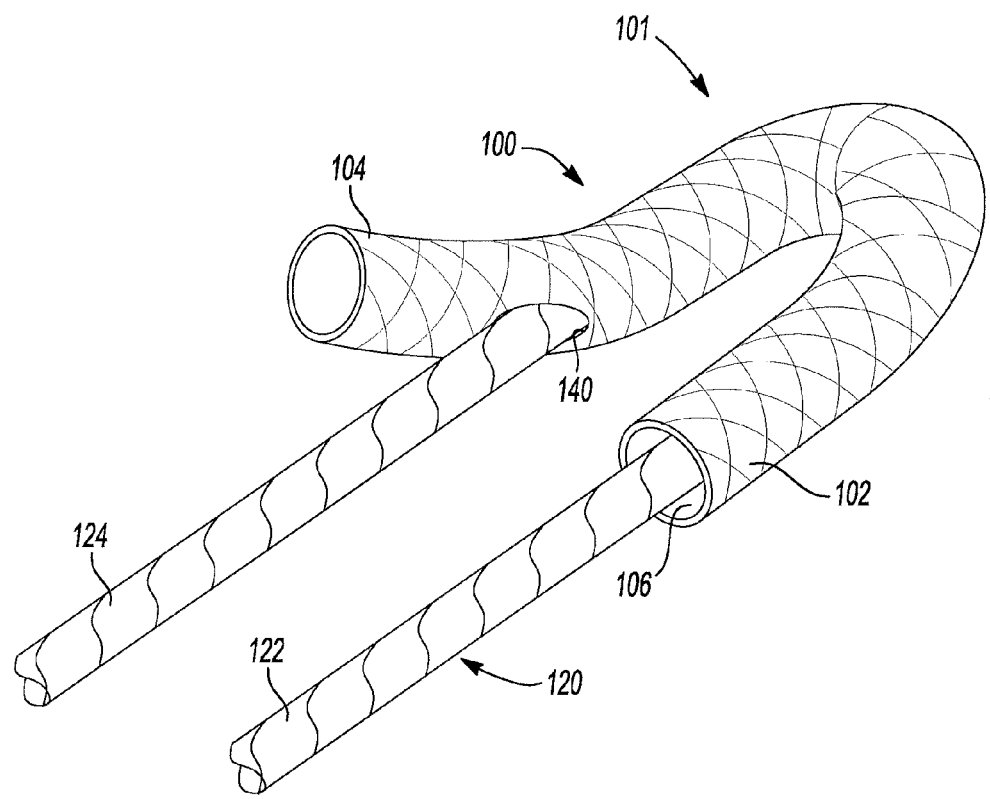
FIG. 1A is a perspective view of a connector device according to the present teachings.
Figure 1B:
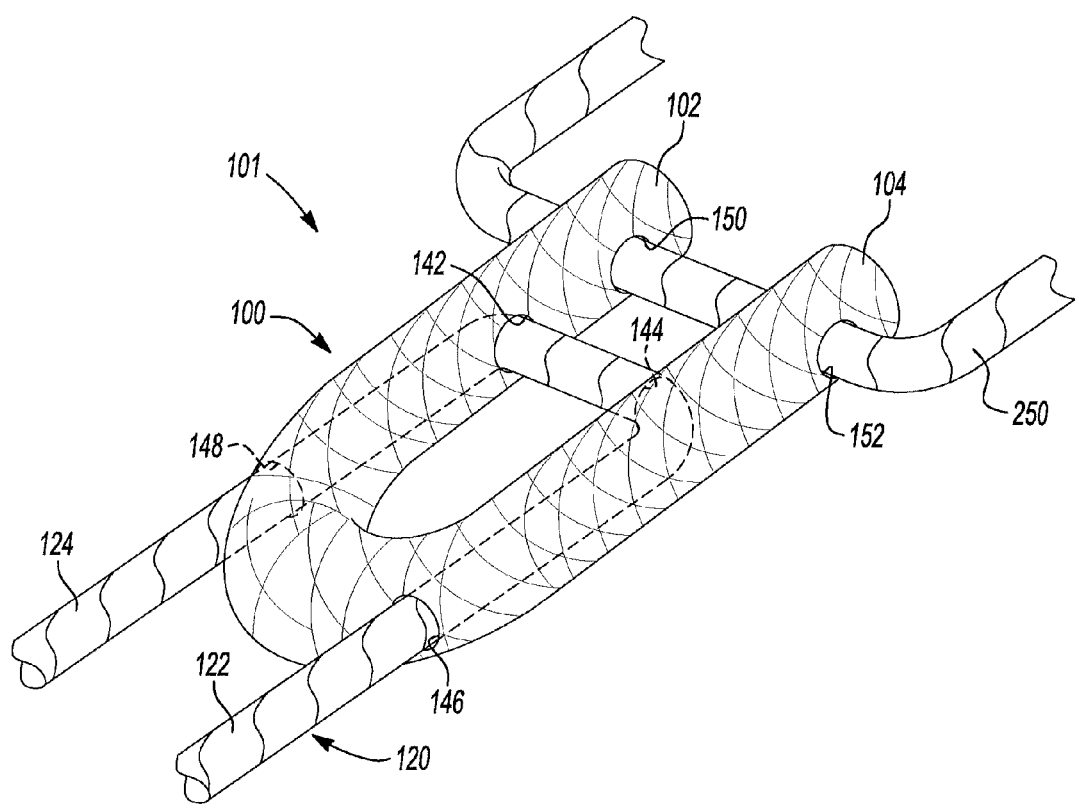
FIG. 1B is a perspective view of another connector device according to the present teachings.
Figure 1C:
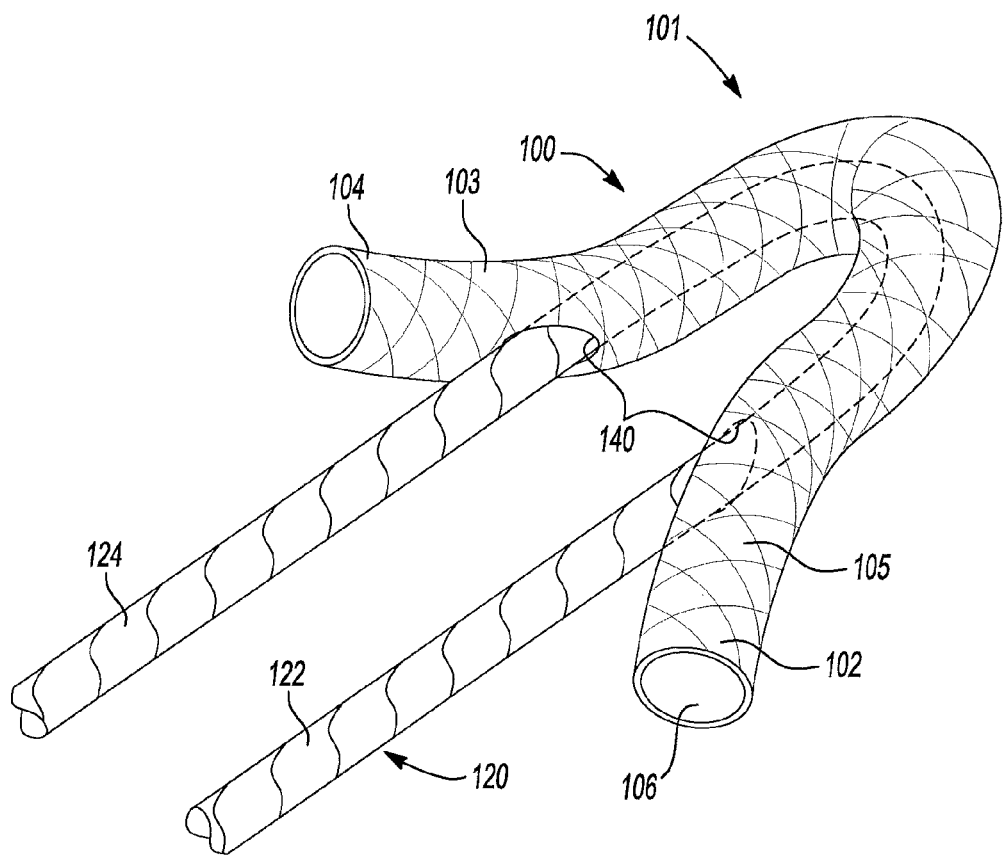
FIG. 1C is a perspective view of another connector device according to the present teachings.

Referring to FIGS. 1, 1A, 1B, and 1C the connector device 101 can also include an elongated flexible strand 120 having first and second ends 122, 124. The strand 120 can pass axially through the bore 106 of the sleeve 100, such that the first and second strand ends 122, 124 exit the corresponding first and second ends 102, 104 of the sleeve 100, as illustrated in FIG. 1. In one aspect, the strand 120 can exit the bore 106 through at least one opening 140 of the sleeve 100 intermediate the first and second ends 102, 104 of the sleeve, as shown in FIG. 1A. In another aspect, the strand 120 can exit the bore 106 through two openings 140 of the sleeve 100 intermediate the first and second ends 102, 104 of the sleeve 100, as shown in FIG. 1C. First and second end portions or sleeve legs 103, 105, are defined between each end 104, 102 and the corresponding opening 140. In another aspect, the strand 120 can pass through openings 142, 144, 146, 148, such that an intermediate portion of the strand 120 is outside the bore 106, as shown in FIG. 1B.

The strand 120 can also be made of materials similar to the sleeve 100, such as braided filaments or fibers of biocompatible material, including natural and synthetic fibers, such as cotton, silk, polymer, polyester, polyethylene, thin wire, suture, and other materials. The strand 120 can also be in the form of a flat tubular suture or a braided suture with or without a core. The connector device 101 with the sleeve 100 and strand 120 are implantable in soft tissue or bone.

Figures 2, 2A:
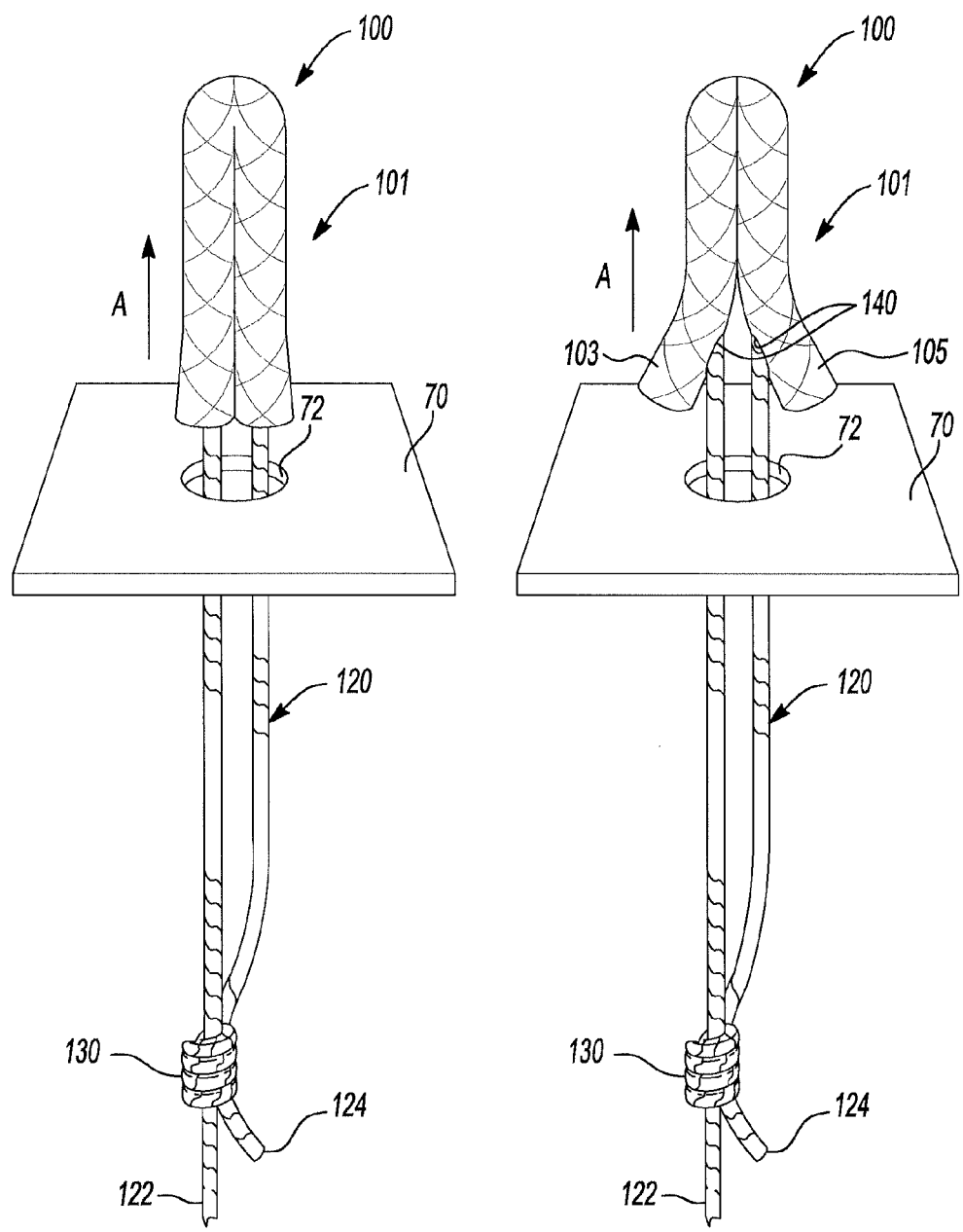
FIG. 2 is a perspective view of the connector device of FIG. 1, shown prior to engagement with a representative aperture.
FIG. 2A is a perspective view of the connector device of FIG. 1C, shown prior to engagement with a representative aperture.

Referring to FIGS. 1-3A, a general procedure for using the connector device 101 is illustrated. The sleeve 100 with the strand 120 therethrough can be folded and pushed through on orifice 72 or other aperture defined through a support 70 in the direction of arrow "A", as shown in FIGS. 2 and 2A. The strand ends of 122, 124 can be connected with a knot 130, such as slipknot, forming a strand loop 128 passing through the bore 106 of the sleeve 100.

Figures 3, 3A:
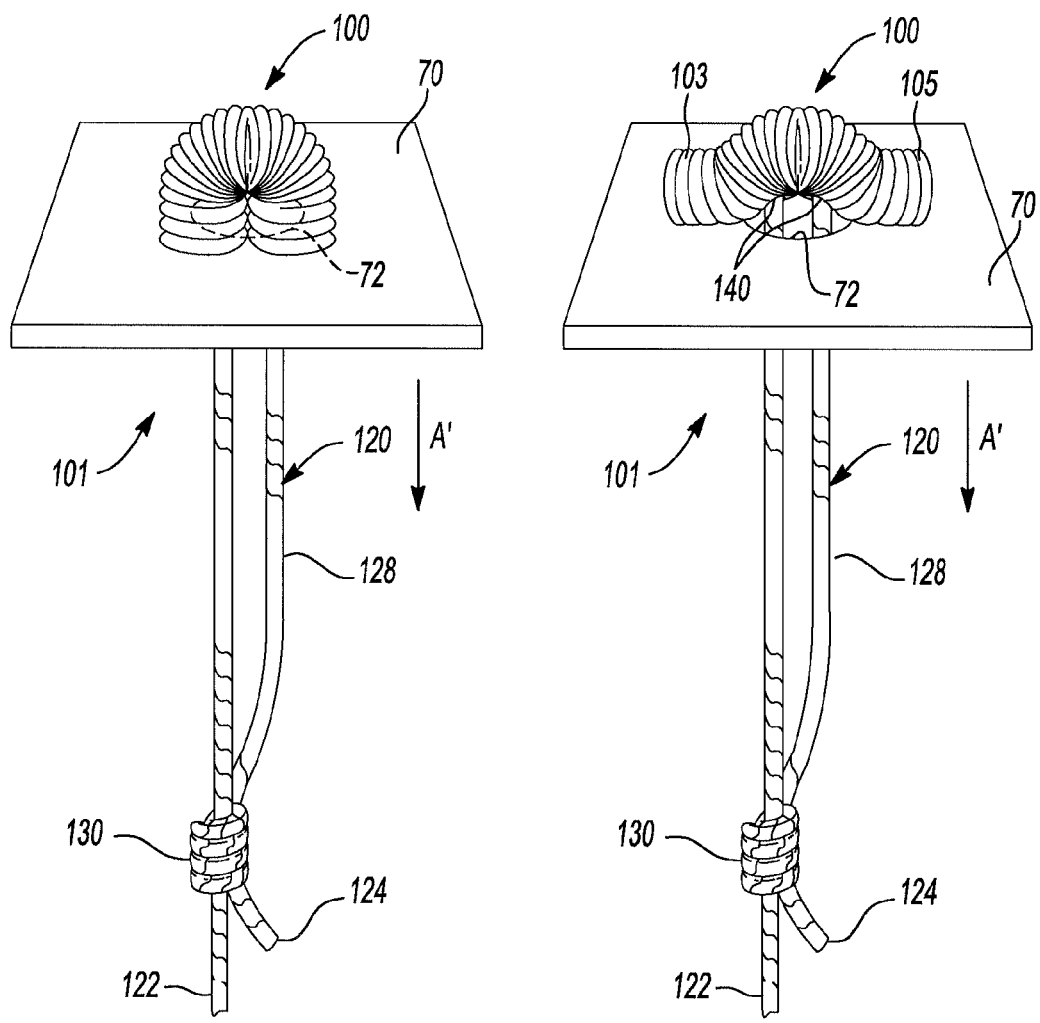
FIG. 3 is a perspective view of the connector device of FIG. 1, shown in engagement with a representative aperture.
FIG. 3A is a perspective view of the connector device of FIG. 1C, shown in engagement with a representative aperture.

Referring to FIGS. 2 and 3, pulling on one of the strand ends 122, 124, shortens the length of the strand loop 128 and the tension causes the sleeve 100 to change configuration, bunching up from a folded and/or flaccid configuration to a bunched-up, ball-like configuration that cannot pass through the orifice 72, such that the strand 120 can be secured on the support 70. In this configuration, the strand ends 122, 124 and the sleeve 100 remain on opposite sides of the orifice 72.

Similarly, and referring to FIGS. 2A and 3A, pulling on one of the strand ends 122, 124, shortens the length of the strand loop 128 and the tension causes the sleeve 100 to change configuration, bunching up from a folded and/or flaccid configuration to a bunched-up bell-like shape with the legs 103, 105 extended outward and pressed against the support 70. In this configuration, the sleeve 100 cannot pass through the orifice 72 in the direction of the arrow A'. The strand ends 122, 124 and the sleeve 100 remain on opposite sides of the orifice 72, and the legs 103, 105 provide additional resistance for securing the strand 120 to the support 70.

The orifice 72 can be of any shape, including any regular or irregular closed curves or polygons, or combination thereof, including circular elliptical, oval, triangular, tetragonal, hexagonal, lobed, or other shapes. The shape and size of the orifice 72 is such that the sleeve 100 in its bent shape deforms sufficiently to slide through the orifice 72 when introduced along one direction A. Once the sleeve 100 passes through and out of the orifice 72 and returns to its undeformed flaccid configuration, the sleeve 100 will bunch up against the orifice 72 when directed or pulled in the opposite direction A', as the ends 102, 104 of the sleeve 100, or the sleeve legs 103, 105, and/or deformed shape are caught against the support 70. It is noted that the strand 120 can still slide relative to the sleeve 100 and the orifice 72, therefore the orifice 72 can act effectively as an anchor eyelet.

The support 70 can be soft tissue, bone, implant, anchor or other threaded or unthreaded implantable fixation member such as those illustrated in FIGS. 5-8 at 200. The fixation members are generically referenced with numeral 200 or specifically with reference numerals 200a-200d. The connector device 101 and the fixation member 200 can form an implantable fixation assembly that can be used for securing soft tissue to bone, as further discussed below in connection with FIG. 9.

It will be appreciated that the connector device 101 can be used as a versatile suture lock that is easy to use, avoids knot-tying, and saves time during the surgical procedure. Further, as the flexible strand 120 is held against the support 70, the flexible strand 120 is prevented from pulling through without being knot-tied to the support 70. It is estimated that the flexible strand 120 can withstand a pulling force greater than that in a knot tied in the same-sized strand.

Any of the connector devices 101 illustrated in FIGS. 1, 1A, 1B, 1C, or combinations thereof, can be used with a fixation member 200 for fastening any type of ligaments, grafts or sutures, and can be used, for example, for rotator cuff repair for the shoulder, for acromioclavicular (AC) joint reconstruction, for tibial graft fixation, for ACL reconstruction, and generally for fastening tendons or grafts and sutures to tissue, including soft tissue and bone. In many of such shoulder repair procedures, a tendon is secured to the bone with many suture anchors requiring repeated knot-tying. Such knot-tying is cumbersome and time consuming during an arthroscopic procedure, as it is generally performed through an insertion cannula that is used to deliver the suture anchor. As discussed below, the connector device 101 illustrated in FIGS. 4 and 9 can be used to secure multiple suture anchors or other fixation members 200 without individual knots for each fixation member 200, and with only one final knot 130 for the entire series of fixation members 200 outside the cannula. Moreover, the knot 130 that forms the single loop 128 of the flexible strand 120 can be pre-tied.

Figure 4:
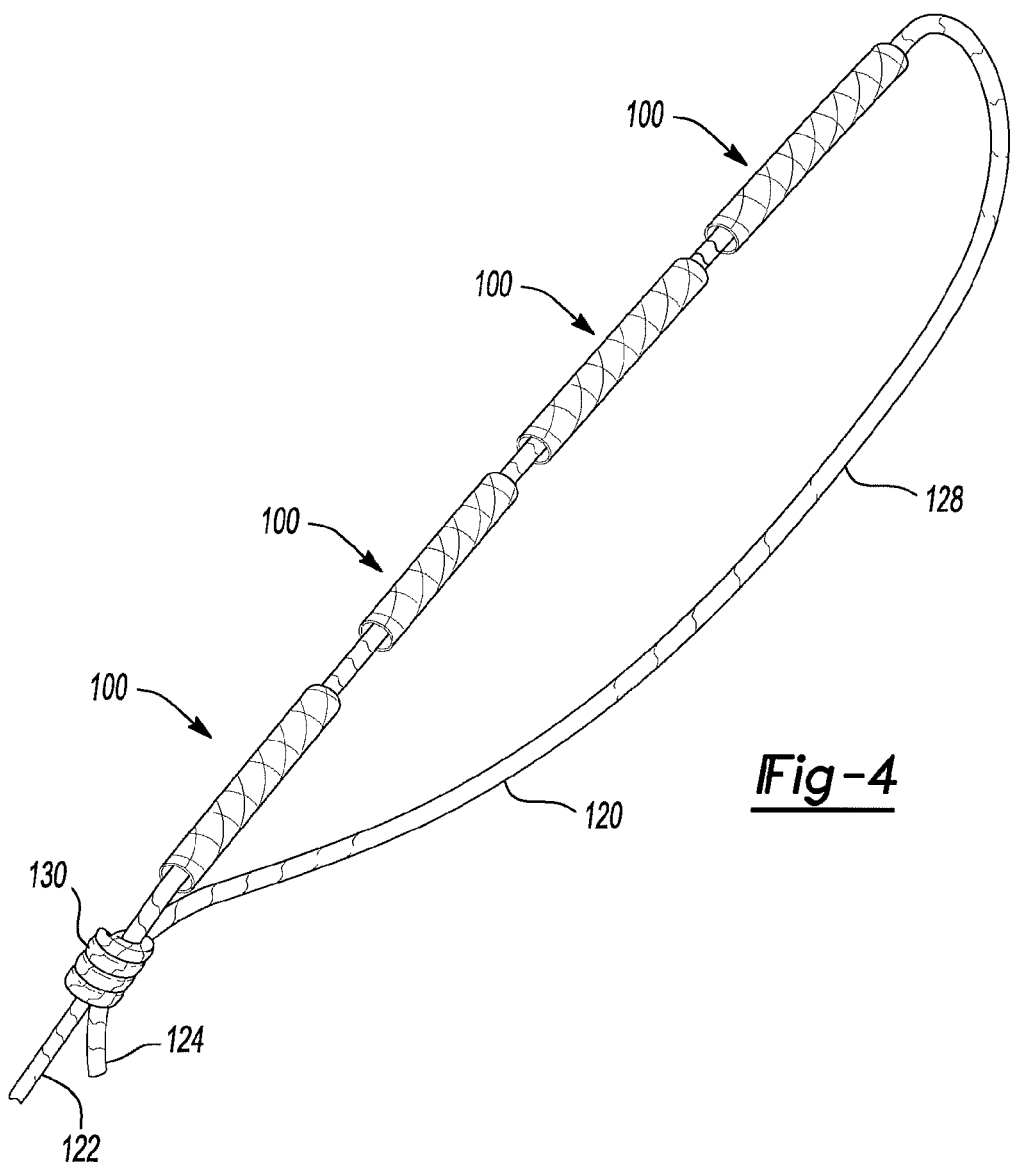
FIG. 4 is a perspective view of a series of interconnected connector devices according to the present teachings.
Figure 9:
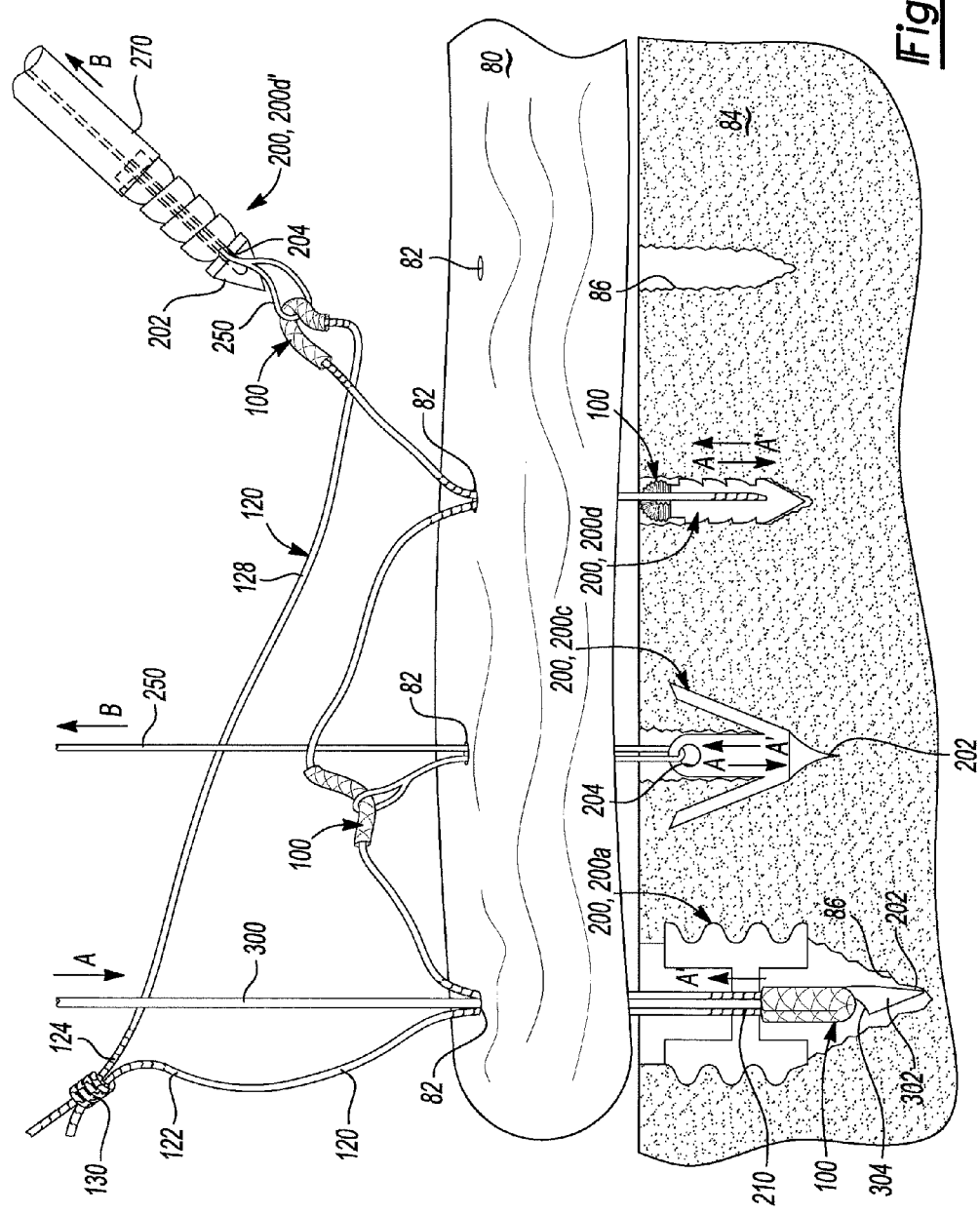
FIG. 9 is an exemplary method of using a series of interconnected connector devices for securing soft tissues to bone.

Referring to FIG. 5, the fixation member 200 can be in the form of an externally threaded open-ended tubular member 200a and can include a body 218 having an open-ended longitudinal bore 212 interrupted by a cross-wall 214. The wall 214 defines a through-slot or other aperture 210 substantially coaxial with the bore 212. The sleeve 100 can pass through the aperture 210 in a folded configuration in the direction of arrow A, while the strand ends 122, 124 of the strand 120 remaining outside the fixation member 200. The sleeve 100 can be held against the wall 214 in a bunched-up (ball or bell-like) configuration when pulled by the strand 120 in the direction A'. In the same manner, a plurality of sleeves 100 strung together in a single loop 128 of a single strand 120, as shown in FIG. 4, can be secured to a corresponding plurality of fixation members 200, without requiring individual knots, as shown in FIG. 9 and discussed below. Using a plurality of sleeves 100 in a single loop 128 allows a fast and efficient procedure of creating a suture mat for attaching soft tissue 80 to bone 84 in multiple locations without having to tie knots arthroscopically through a cannula for each individual fixation member 200.

Referring to FIG. 6, the fixation member 200 can be an implant in the form of a tubular anchor 200b having a body 218 and include a longitudinal bore 212 closed at one end with a pointed anchoring tip 202. The anchoring tip 202 can be integrally or removably coupled to the body 218. The anchoring tip 202 can include a longitudinal extension 216 received in the bore 212. The extension 216 can define an aperture 210 substantially parallel with the bore 212. The sleeve 100 can be passed through the aperture 210 in the direction of arrow A, such that the strand 120 passes through the aperture 210, through the bore 212 and exits the fixation member 200. The sleeve 100 can be held between a wall of the bore 212 and the extension 216 in a bunched-up (ball or bell-like) configuration after the strand 120 is pulled away from the fixation member 200 in another direction, such as the direction of arrow A'. It should be appreciated that the directions A and A' need not be opposite. Pulling in any direction A' that will cause the strand 120 to tension can suffice. Although FIGS. 5 and 6 illustrate examples of an aperture 210 that is respectively coaxially or perpendicularly oriented relative to the bore 212 of the fixation member 200, it will be appreciated that the aperture 210 is not limited to these orientations. The fixation member 200b can also be used in a single loop 128 with multiple similar or different fixation members 200 for attaching soft tissue 80 to bone 84 in multiple locations, as illustrated in FIG. 9.

Referring to FIG. 7, the fixation member 200 can be an implant in the form of harpoon-type anchor 200c having a pointed anchoring tip 202. The fixation member 200 can include a central body 218 defining an aperture 210. The sleeve 100 can be passed through the aperture 210 in the direction of arrow A. The strand 120 can form a loop 128 passing through the aperture 210 in the direction of arrow A. The strand ends 122, 124 can be pulled away from the fixation member 200 in the direction of arrow A', such that the sleeve 100 is held against the body 218 in a bunched-up (ball or bell-like) configuration. The fixation member 200c can also be used in a single loop 128 with multiple similar or different fixation members 200 for attaching soft tissue 80 to bone 84 in multiple locations, as illustrated in FIG. 9.

Referring to FIG. 8, the fixation member 200 can be an implant in the form of an externally threaded suture anchor 200d having a body 218 with an anchoring tip 202 and including a longitudinal bore 212 extending from a proximal end 206 to a distal eyelet 204. The sleeve 100 can be passed through the eyelet 204, the bore 212 and the aperture 210 defined at proximal end 206 of the bore 212 in the direction of arrow A. The strand 120 can form a loop 128 passing through the bore 212 and exiting the eyelet 204. The strand ends 122, 124 can be pulled away from the fixation member 200 in the direction of arrow A', such that the sleeve 200 can be secured against the proximal end 206 in a bunched-up (ball or bell-like) configuration. The fixation member 200d can also be used in a single loop 128 with multiple similar or different fixation members 200 for attaching soft tissue 80 to bone 84 in multiple locations, as illustrated in FIG. 9.

The connector device 101 can be pushed through the aperture in the fixation member 200 using an inserter, such as the inserter 300 shown in FIG. 9 and the inserter described and shown in FIGS. 8A-9B and 13-15 of the cross-referenced patent application Ser. No. 11/347,661 filed on Feb. 3, 2006, although other inserters can also be used. The sleeves 100 of the connector device 101 can be coupled to corresponding fixation members 200, either before or after the fixation members 200 are secured in the bone 84.

Referring to FIGS. 4 and 9, a series of sleeves 100 can be strung along a single loop or chain 128 of the strand 120 without other knots except a single slipknot 130 coupling the strand ends 122, 1224. Each sleeve 100 can be inserted in a corresponding prepared bone bore 84 or in a corresponding fixation member 200 to attach soft tissue 80 to a bone 84. It will be appreciated that identical or different fixation members 200, such as, for example, fixation members 200a-200d, can be used for securing the corresponding sleeves 100, and one or more fixation members 200 can be omitted, such that the sleeve 100 is secured directly in a bone bore 86 without using a fixation member 200. Some exemplary options are illustrated in a single illustration in FIG. 9.

It will be appreciated that the sleeve 100 can be inserted or secured to the fixation member 200 either before or after the fixation member 200 has been implanted into the bone 84. For example, the sleeve 100 can be secured to the fixation member 200 prior to bone implantation, either manually or by using an inserter, such as the inserter 300 that includes a tip 302 and a hook 304 in which the sleeve can be supported in a folded, U-shape configuration with the strand 120 therethrough. Alternatively, and as illustrated in FIG. 9 in connection with the fixation member 200a, the fixation member 200a can first be implanted into bone 84. The tip 302 of the inserter 300 with the sleeve 100 thereon can be pushed through the aperture 210 of the fixation member 200a in the direction of arrow A.

Referring to FIG. 9 and in connection with the exemplary fixation member 200c, another method of securing the sleeve 100 to the fixation member 200c, after the fixation member 200c is implanted, is illustrated. Specifically, an auxiliary flexible member or string 250 in the form of a monofilament made of polyethylene, polyester, silk, or other biocompatible fiber or thin string-like material can be looped around the sleeve 100 and passed through the aperture 210 of the fixation member 200c. Pulling the auxiliary member 250 in the direction of arrow "B" causes the sleeve 100 and portion of the strand 120 to pass through the aperture 210 in a folded configuration. The auxiliary member 250 can be then pulled out and completely removed from the sleeve 100 and fixation member 200c. The sleeve 100 can be secured to the fixation member 200c in a bunched-up (ball or bell-like) configuration by pulling one the ends 122, 124 of the strand loop 128 to shorten the loop 128, as described above. In another aspect, the auxiliary flexible member 250 can be looped through openings 150, 152 of the sleeve 100, as shown in FIG. 1B.

With continued reference to FIG. 9, fixation member 200d is shown implanted in bone bore 86 with the sleeve 100 shown in a bunched-up (ball or bell-like) configuration. Another fixation member 200d' is illustrated before implantation into the bone bore 86. The fixation member 200d' can be coupled to a cannulated or other fixation-member inserter 270 for insertion through an incision or other opening 82 in soft tissue 80 and into a bone bore 86. The opening 82 can be pre-formed with another surgical instrument or by the pointed tip 202 of the fixation member 200d' as it is pushed through the soft tissue 80. Similarly, the bone bore 86 can be pre-formed, or created by the threaded fixation member 200d' as it is threadably inserted into the bone 84. An auxiliary member 250 can be used to manipulate the sleeve 100 and secure the sleeve 100 into the fixation member 200d', as described above in connection with fixation member 200c. The auxiliary member 250 can be looped around the sleeve 100 and passed through the eyelet 204 into the bore 212 and out of the aperture 210 at the proximal end 206. The sleeve 100 can be pulled through the eyelet 204, the bore 212 and aperture 210 by pulling the auxiliary member 250 in the direction of the arrow B either before or after implantation of the fixation member 200d' into the bone 84.

After all the sleeves 100 have been secured to the corresponding fixation members 200, the single loop 128 is tightened by pulling one of the strand ends 122, 124 relative to slipknot 130. In this manner, tissue to tissue attachment in multiple locations without the need of individual knots for each location is conveniently performed, thus avoiding the need of tying individual knots through cannulas for each fixation member 200. The procedure can be used for any tissue to tissue attachment, including, but not limited to, various arthroscopic procedures, such as, for example, rotator cuff repair, acromioclavicular reconstruction, and other procedures for which multiple anchor fixation can be beneficial. The procedure can be performed efficiently by simply passing by pulling or pushing the connector device 101 through an aperture or eyelet of the anchor or other fixation member 200 in one direction and then tensioning or pulling the strand 120 of the connector device 101 in the another direction for a knotless attachment of the strand 120 to the fixation member 200. The pull-out strength of the attachment can be a function of the strand size, but greater than using a mere strand with a knot.

Generally, and described above, the connector device 101 including one or more sleeves 100 can be to secure a strand 120, such as a suture to soft tissue 80 or bone, and to attach soft tissue to bone. Any of the connector devices 101 illustrated in FIGS. 1, 1A, 1B and 1C, can be used with or without a fixation member 200 and with or without an inserter 300 and with or without an auxiliary member 250 for manipulation the sleeve 100, although only the connector 101 of FIG. 1 is shown in the exemplary illustrations of FIGS. 4-9. Accordingly, a fixation assembly kit can be provided that includes, for example, a plurality of sleeves 100, a cartridge of continuous stand 120 or separate pieces of strand 120, a cartridge or separate pieces of auxiliary member material, one or more inserters, various fixation members 200, and one or more fixation member inserters 270. The sleeves 100 and strand 120 can be provided preloaded on one or more inserters 300. When a fixation member 200 is used, the fixation member 200 can be provided preloaded on a fixation member inserter 270. The connector device 101 allows tissue to tissue attachment in multiple locations without the need of individual knots for each location. After multiple-location attachment is performed, the single loop 128 is tightened by pulling one of the strand ends 122, 124 relative to slipknot 130.

The foregoing discussion discloses and describes merely exemplary arrangements. One skilled in the art will readily recognize from such discussion, and from the accompanying drawings and claims, that various changes, modifications and variations can be made therein without departing from the spirit and scope of the present teachings as defined in the following claims.

What is claimed is:

1. A method for securing a strand to a bone with at least one fixation member for a surgical procedure comprising:
    passing an elongated flexible strand having first and second ends through a longitudinal bore of a flexible sleeve such that the first and second ends of the flexible strand are outside the flexible sleeve;
    folding the sleeve into a first U-shaped configuration;
    pushing the sleeve completely through a longitudinal aperture of the fixation member in a first direction in the first U-shaped configuration; and tensioning the strand to change the sleeve to a second configuration that cannot pass through the aperture of the fixation member by pulling the sleeve in the second direction.

2. The method of claim 1, wherein the sleeve has first and second ends and the first and second ends of the strand exit the sleeve from corresponding first and second openings intermediate the first and second ends of the sleeve.

3. The method of claim 1, wherein pushing the sleeve through the aperture of the fixation member comprises:
    loading the sleeve on an inserter;
    pushing the inserter through the aperture in the first direction; and
    removing the inserter.

4. The method of claim 1, further comprising inserting the fixation member into the bone.

5. The method of claim 1, further comprising:
    making a hole in the bone; and
    inserting the fixation member into the hole.

6. The method of claim 1, wherein changing the sleeve to the second configuration includes pressing first and second end portions of the sleeve against the fixation member.

7. The method of claim 1, wherein changing the sleeve to the second configuration includes deforming the sleeve to a bell-like shape.

8. The method of claim 1, further comprising pushing the sleeve through the aperture of the fixation member after inserting the fixation member into the bone.

9. The method of claim 1, further comprising inserting the fixation member in a pre-formed bore in the bone.

10. The method of claim 1, further comprising threading the fixation member into the bone.

11. The method of claim 1, further comprising:
    connecting the first and second ends of the flexible strand with a single knot; and
    forming an adjustable loop terminating at the knot.

12. The method of claim 11, further comprising pulling one end of the flexible strand relative to the knot and reducing the length of the loop.

13. A method for securing a strand to a bone with a bone anchor for a surgical procedure, the method comprising:
    inserting a first bone anchor into a bone;
    passing a strand having first and second ends through a plurality of longitudinal bores of a corresponding plurality of flexible sleeves serially coupled on the strand;
    folding a first sleeve of the plurality of flexible sleeves in a first U-shape configuration; pushing the first sleeve in the first U-shape configuration completely through an aperture of the first bone anchor in a first direction;
    deforming the first sleeve to a second configuration that cannot pass through the aperture; and
    connecting the first and second ends of the strand with a single knot.

14. The method of claim 13, wherein deforming the first sleeve to a second configuration includes pressing first and second end portions of the first sleeve against the first bone anchor.

15. The method of claim 13, further comprising deforming the first sleeve to a bell-like shape.

16. The method of claim 13, further comprising:
    forming a loop relative to the first sleeve with an auxiliary flexible member having first and second ends:
    passing the first and second ends of the auxiliary member through the aperture of the first bone anchor in the first direction;
    pulling the first and second ends of the auxiliary member through the aperture of the first bone anchor until the first sleeve passes through the aperture; and
    removing the auxiliary flexible member.

17. The method of claim 13, further comprising inserting the first bone anchor into a pre-formed bore in the bone.

18. The method of claim 13, further comprising threading the first bone anchor into the bone.

19. The method of claim 13, further comprising forming an adjustable loop terminating at the single knot.

20. The method of claim 19, further comprising pulling one end of the strand relative to the single knot and reducing the length of the loop.

21. The method of claim 13, wherein the single knot is a slipknot and the method further comprises:
   passing the strand through a plurality of locations of a soft tissue adjacent to the bone;
   tensioning the strand; and
   securing the soft tissue to the bone with the single slipknot.

22. The method of claim 13, further comprising passing the remaining sleeves of the plurality of flexible sleeves through corresponding apertures of corresponding bone anchors in a first direction.

23. A method for securing a strand to a bone for a surgical procedure comprising:
   passing a strand slidably through a plurality of flexible sleeves;
   forming a single slipknot on a portion of the strand outside all the plurality of flexible sleeves, the slipknot forming a closed loop;
   folding a first sleeve of the plurality of flexible sleeves in a first U-shape; pushing the first sleeve completely through an aperture of a first bone anchor in the first U-shape in a first direction;
   deforming the first sleeve to a second shape that cannot pass through the aperture; and
   reducing a length of the loop.

24. The method of claim 23, wherein deforming the first sleeve to a second shape that cannot pass through the aperture includes:
   allowing the first sleeve to return to a flaccid shape;
   pulling the first sleeve in a second direction opposite to the first direction;
   pressing a first and second end portions of the first sleeve against the first bone anchor; and
   deforming the first sleeve to a bell-like shape.

25. The method of claim 23, further comprising passing the remaining sleeves of the plurality of flexible sleeves through corresponding apertures of corresponding bone anchors in a first direction.

* * * * *